US008439245B2

(12) United States Patent
Knodel et al.

(10) Patent No.: US 8,439,245 B2
(45) Date of Patent: *May 14, 2013

(54) TRUE MULTI-FIRE ENDOCUTTER

(75) Inventors: Bryan D. Knodel, Flagstaff, AZ (US);
Bernard A. Hausen, Redwood City, CA (US); Luke W. Clauson, Redwood City, CA (US)

(73) Assignee: Cardica, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/194,098

(22) Filed: Jul. 29, 2011

(65) Prior Publication Data
US 2011/0284613 A1 Nov. 24, 2011

Related U.S. Application Data

(62) Division of application No. 11/851,379, filed on Sep. 6, 2007, now Pat. No. 7,988,026.

(51) Int. Cl.
*A61B 17/064* (2006.01)
*A61B 17/072* (2006.01)

(52) U.S. Cl.
USPC ............. 227/175.1; 227/19; 606/219

(58) Field of Classification Search .... 227/175.1–182.1, 227/19; 606/219
See application file for complete search history.

(56) References Cited

U.S. PATENT DOCUMENTS

| 1,939,631 | A | 12/1933 | Randall |
|---|---|---|---|
| 1,947,388 | A | 2/1934 | Frey |
| 2,127,665 | A | 8/1938 | Leslie |
| 2,568,969 | A | 9/1951 | Reiss et al. |
| 3,086,208 | A | 4/1963 | Eby |
| 3,254,650 | A | 6/1966 | Collito |
| 3,254,651 | A | 6/1966 | Collito |

(Continued)

FOREIGN PATENT DOCUMENTS

| DE | 69406845 | 4/1998 |
|---|---|---|
| DE | 19732234 | 1/1999 |

(Continued)

OTHER PUBLICATIONS

"Atlas of Surgical Stapling", *Ethicon Endo-Surgery*, (1999).

(Continued)

*Primary Examiner* — Lindsay Low
(74) *Attorney, Agent, or Firm* — Cardica, Inc.

(57) ABSTRACT

An exemplary surgical endocutter may include a staple holder; at least one feeder belt having two lateral edges, at least part of at least one feeder belt extending into the staple holder; and staples, wherein each said staple may include a first end frangibly affixed to a corresponding feeder belt, wherein each first end is affixed to the feeder belt at a location laterally spaced from the longitudinal centerline of the feeder belt, and a second free end; and wherein the staples form at least one row, each row including at least two said staples; wherein staples in least one row are staggered relative to said staples in at least one other row. Another exemplary surgical endocutter may include a feeder belt; staples frangibly connected to the feeder belt; and at least one wedge movable relative to the staples in a direction substantially longitudinal relative to the feeder belt; wherein at least one wedge both directly engages a plurality of staples and disconnects a plurality of staples from the feeder belt in a single continuous motion of the wedge.

5 Claims, 22 Drawing Sheets

U.S. PATENT DOCUMENTS

| | | |
|---|---|---|
| 3,519,187 A | 7/1970 | Kapitanov et al. |
| 3,581,551 A | 6/1971 | Wilkinson |
| 3,618,842 A | 11/1971 | Bryan |
| 3,650,453 A | 3/1972 | Smith, Jr. |
| 3,675,688 A | 7/1972 | Bryan et al. |
| 3,717,294 A | 2/1973 | Green |
| 3,774,615 A | 11/1973 | Lim et al. |
| 3,795,034 A | 3/1974 | Strekopytov et al. |
| 3,837,555 A | 9/1974 | Green |
| 3,899,914 A | 8/1975 | Akiyama |
| 3,949,924 A | 4/1976 | Green |
| 3,955,581 A | 5/1976 | Spasiano et al. |
| 4,043,504 A | 8/1977 | Hueil et al. |
| 4,076,162 A | 2/1978 | Kapitanov et al. |
| 4,086,926 A | 5/1978 | Green et al. |
| 4,127,227 A | 11/1978 | Green |
| 4,214,587 A | 7/1980 | Sakura, Jr. |
| 4,228,895 A | 10/1980 | Larkin |
| 4,241,861 A | 12/1980 | Fleischer |
| 4,248,267 A | 2/1981 | Brandenberg |
| 4,275,813 A | 6/1981 | Noiles et al. |
| 4,317,451 A | 3/1982 | Cerwin et al. |
| 4,318,313 A | 3/1982 | Tartaglia |
| 4,331,277 A | 5/1982 | Green |
| 4,350,160 A | 9/1982 | Kolesov et al. |
| 4,352,358 A | 10/1982 | Angelchik |
| 4,354,628 A | 10/1982 | Green |
| 4,366,819 A | 1/1983 | Kaster |
| 4,368,736 A | 1/1983 | Kaster |
| 4,475,679 A | 10/1984 | Fleury, Jr. |
| 4,485,811 A | 12/1984 | Chernousov et al. |
| 4,503,568 A | 3/1985 | Madras |
| 4,523,592 A | 6/1985 | Daniel |
| 4,523,707 A | 6/1985 | Blake, III et al. |
| 4,553,542 A | 11/1985 | Schenck et al. |
| 4,556,058 A | 12/1985 | Green |
| 4,589,416 A | 5/1986 | Green |
| 4,593,693 A | 6/1986 | Schenck |
| 4,603,693 A | 8/1986 | Conta et al. |
| 4,605,001 A | 8/1986 | Rothfuss et al. |
| 4,607,637 A | 8/1986 | Berggren et al. |
| 4,617,928 A | 10/1986 | Alfranca |
| 4,624,255 A | 11/1986 | Schenck et al. |
| 4,624,257 A | 11/1986 | Berggren et al. |
| 4,633,861 A | 1/1987 | Chow et al. |
| 4,633,874 A | 1/1987 | Chow et al. |
| 4,655,222 A | 4/1987 | Florez et al. |
| 4,657,019 A | 4/1987 | Walsh et al. |
| 4,665,906 A | 5/1987 | Jervis |
| 4,719,917 A | 1/1988 | Barrows et al. |
| 4,747,407 A | 5/1988 | Liu et al. |
| 4,752,024 A | 6/1988 | Green et al. |
| 4,762,260 A | 8/1988 | Richards et al. |
| 4,773,420 A | 9/1988 | Green |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,938,408 A | 7/1990 | Bedi |
| 4,951,861 A | 8/1990 | Schulze et al. |
| 4,969,591 A | 11/1990 | Richards et al. |
| 4,978,049 A | 12/1990 | Green |
| 5,005,749 A | 4/1991 | Aranyi |
| 5,018,657 A | 5/1991 | Pedlick et al. |
| 5,062,842 A | 11/1991 | Tiffany |
| 5,104,025 A | 4/1992 | Main et al. |
| 5,119,983 A | 6/1992 | Green et al. |
| 5,156,310 A | 10/1992 | Biedenharn |
| 5,156,315 A | 10/1992 | Green et al. |
| 5,156,613 A | 10/1992 | Sawyer |
| 5,156,619 A | 10/1992 | Ehrenfeld |
| 5,170,925 A | 12/1992 | Madden et al. |
| 5,172,845 A | 12/1992 | Tejeiro |
| 5,178,634 A | 1/1993 | Ramos Martinez |
| 5,192,288 A | 3/1993 | Thompson et al. |
| 5,193,731 A | 3/1993 | Aranyi |
| 5,205,459 A | 4/1993 | Brinkerhoff et al. |
| 5,211,683 A | 5/1993 | Maginot |
| 5,219,353 A | 6/1993 | Garvey, III et al. |
| 5,234,447 A | 8/1993 | Kaster et al. |
| 5,242,457 A | 9/1993 | Akopov et al. |
| 5,250,058 A | 10/1993 | Miller et al. |
| 5,269,792 A | 12/1993 | Kovac et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,300,065 A | 4/1994 | Anderson |
| 5,304,220 A | 4/1994 | Maginot |
| 5,307,976 A | 5/1994 | Olson et al. |
| 5,314,435 A | 5/1994 | Green et al. |
| 5,314,468 A | 5/1994 | Ramos Martinez |
| 5,333,773 A | 8/1994 | Main et al. |
| 5,336,233 A | 8/1994 | Chen |
| 5,350,104 A | 9/1994 | Main et al. |
| 5,364,001 A | 11/1994 | Bryan |
| 5,364,389 A | 11/1994 | Anderson et al. |
| 5,366,462 A | 11/1994 | Kaster et al. |
| 5,376,095 A | 12/1994 | Ortiz |
| 5,392,979 A | 2/1995 | Green et al. |
| 5,395,030 A | 3/1995 | Kuramoto et al. |
| 5,413,272 A | 5/1995 | Green et al. |
| 5,415,334 A | 5/1995 | Williamson, IV et al. |
| 5,417,361 A | 5/1995 | Williamson, IV |
| 5,431,322 A | 7/1995 | Green et al. |
| 5,443,497 A | 8/1995 | Venbrux |
| 5,447,513 A * | 9/1995 | Davison et al. ............... 606/143 |
| 5,447,514 A | 9/1995 | Gerry et al. |
| 5,452,836 A | 9/1995 | Huitema et al. |
| 5,454,825 A | 10/1995 | Van Leeuwen |
| 5,456,400 A | 10/1995 | Shichman et al. |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,465,896 A | 11/1995 | Allen et al. |
| 5,476,206 A | 12/1995 | Green |
| 5,478,003 A | 12/1995 | Green et al. |
| 5,478,354 A | 12/1995 | Tovey et al. |
| 5,489,058 A | 2/1996 | Plyley et al. |
| 5,507,776 A | 4/1996 | Hempel |
| 5,522,834 A | 6/1996 | Fonger et al. |
| 5,527,319 A | 6/1996 | Green et al. |
| 5,533,661 A | 7/1996 | Main et al. |
| 5,535,935 A | 7/1996 | Vidal et al. |
| 5,540,677 A | 7/1996 | Sinofsky |
| 5,547,117 A | 8/1996 | Hamblin et al. |
| 5,547,474 A | 8/1996 | Kloeckl et al. |
| 5,553,765 A | 9/1996 | Knodel et al. |
| 5,558,667 A | 9/1996 | Yarborough et al. |
| 5,562,241 A | 10/1996 | Knodel et al. |
| 5,571,167 A | 11/1996 | Maginot |
| 5,580,067 A | 12/1996 | Hamblin et al. |
| 5,586,711 A | 12/1996 | Plyley et al. |
| 5,605,572 A | 2/1997 | Berger |
| 5,609,285 A | 3/1997 | Grant et al. |
| 5,611,794 A | 3/1997 | Sauer et al. |
| 5,620,289 A | 4/1997 | Curry |
| 5,620,452 A | 4/1997 | Yoon |
| 5,626,585 A | 5/1997 | Mittelstadt et al. |
| 5,630,541 A | 5/1997 | Williamson, IV et al. |
| 5,632,432 A | 5/1997 | Schulze et al. |
| 5,632,433 A | 5/1997 | Grant et al. |
| 5,636,780 A | 6/1997 | Green |
| 5,643,340 A | 7/1997 | Nunokawa |
| 5,653,373 A | 8/1997 | Green et al. |
| 5,655,698 A | 8/1997 | Yoon |
| 5,657,921 A | 8/1997 | Young et al. |
| 5,662,258 A | 9/1997 | Knodel et al. |
| 5,662,259 A | 9/1997 | Yoon |
| 5,662,260 A | 9/1997 | Yoon |
| 5,665,085 A | 9/1997 | Nardella |
| 5,669,544 A | 9/1997 | Schulze et al. |
| 5,669,918 A | 9/1997 | Balazs et al. |
| 5,669,934 A | 9/1997 | Sawyer |

| | | |
|---|---|---|
| 5,673,840 A | 10/1997 | Schulze et al. |
| 5,676,670 A | 10/1997 | Kim |
| 5,692,668 A | 12/1997 | Schulze et al. |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,369 A | 1/1998 | Vaitekunas et al. |
| 5,707,380 A | 1/1998 | Hinchliffe et al. |
| 5,709,693 A | 1/1998 | Taylor |
| 5,711,472 A | 1/1998 | Bryan |
| 5,725,544 A | 3/1998 | Rygaard |
| 5,749,895 A | 5/1998 | Sawyer et al. |
| 5,752,965 A | 5/1998 | Francis et al. |
| 5,776,130 A | 7/1998 | Buysse et al. |
| 5,797,920 A | 8/1998 | Kim |
| 5,799,857 A | 9/1998 | Robertson et al. |
| 5,810,855 A | 9/1998 | Rayburn et al. |
| 5,816,471 A | 10/1998 | Plyley et al. |
| 5,817,113 A | 10/1998 | Gifford, III et al. |
| 5,824,015 A | 10/1998 | Sawyer |
| 5,827,265 A | 10/1998 | Glinsky et al. |
| 5,827,271 A | 10/1998 | Buysse et al. |
| 5,833,690 A | 11/1998 | Yates et al. |
| 5,833,695 A * | 11/1998 | Yoon ............................ 606/139 |
| 5,833,698 A | 11/1998 | Hinchliffe et al. |
| 5,855,311 A | 1/1999 | Hamblin et al. |
| 5,865,730 A | 2/1999 | Fox et al. |
| 5,871,135 A | 2/1999 | Williamson, IV et al. |
| 5,875,538 A | 3/1999 | Kish et al. |
| 5,878,938 A | 3/1999 | Bittner et al. |
| 5,879,371 A | 3/1999 | Gardiner et al. |
| 5,893,369 A | 4/1999 | Lemole |
| 5,894,979 A | 4/1999 | Powell |
| 5,904,697 A | 5/1999 | Gifford, III et al. |
| 5,913,866 A | 6/1999 | Ginn et al. |
| 5,915,616 A | 6/1999 | Viola et al. |
| 5,918,791 A | 7/1999 | Sorrentino et al. |
| 5,921,995 A | 7/1999 | Kleshinski |
| 5,944,730 A | 8/1999 | Nobles et al. |
| 5,964,774 A | 10/1999 | McKean et al. |
| 5,976,159 A | 11/1999 | Bolduc |
| 5,993,464 A | 11/1999 | Knodel |
| 5,993,476 A | 11/1999 | Groiso |
| 6,004,335 A | 12/1999 | Vaitekunas et al. |
| 6,015,416 A | 1/2000 | Stefanchik et al. |
| 6,024,748 A | 2/2000 | Manzo et al. |
| 6,036,700 A | 3/2000 | Stefanchik et al. |
| 6,039,733 A | 3/2000 | Buysse et al. |
| 6,039,773 A | 3/2000 | Cherpeck |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |
| 6,071,289 A | 6/2000 | Stefanchik et al. |
| 6,083,234 A | 7/2000 | Nicholas et al. |
| 6,086,304 A | 7/2000 | Hujishima et al. |
| 6,110,187 A | 8/2000 | Donlon |
| 6,117,148 A | 9/2000 | Ravo et al. |
| 6,176,413 B1 | 1/2001 | Heck et al. |
| 6,183,486 B1 | 2/2001 | Snow et al. |
| 6,187,019 B1 | 2/2001 | Stefanchik |
| 6,193,129 B1 | 2/2001 | Bittner et al. |
| 6,193,734 B1 | 2/2001 | Bolduc et al. |
| 6,200,263 B1 | 3/2001 | Person |
| 6,209,773 B1 | 4/2001 | Bolduc et al. |
| 6,248,117 B1 | 6/2001 | Blatter |
| 6,254,617 B1 | 7/2001 | Spence et al. |
| 6,264,087 B1 | 7/2001 | Whitman |
| 6,280,460 B1 | 8/2001 | Bolduc et al. |
| 6,306,149 B1 | 10/2001 | Meade |
| 6,391,038 B2 | 5/2002 | Vargas et al. |
| 6,394,948 B1 | 5/2002 | Borst et al. |
| 6,419,682 B1 | 7/2002 | Appleby et al. |
| 6,436,097 B1 | 8/2002 | Nardella |
| 6,443,973 B1 | 9/2002 | Whitman |
| 6,461,365 B2 | 10/2002 | Bolduc et al. |
| 6,478,804 B2 | 11/2002 | Vargas et al. |
| 6,514,263 B1 | 2/2003 | Stefanchik et al. |
| 6,520,973 B1 | 2/2003 | McGarry |
| 6,530,932 B1 | 3/2003 | Swayze |
| 6,551,334 B2 | 4/2003 | Blatter et al. |
| 6,569,173 B1 | 5/2003 | Blatter et al. |
| 6,592,597 B2 | 7/2003 | Grant et al. |
| 6,602,252 B2 | 8/2003 | Mollenauer |
| 6,623,494 B1 | 9/2003 | Blatter |
| 6,626,921 B2 | 9/2003 | Blatter et al. |
| 6,652,542 B2 | 11/2003 | Blatter et al. |
| 6,663,590 B2 | 12/2003 | Blatter |
| 6,698,643 B2 | 3/2004 | Whitman |
| 6,716,232 B1 | 4/2004 | Vidal et al. |
| 6,722,552 B2 | 4/2004 | Fenton, Jr. |
| 6,726,694 B2 | 4/2004 | Blatter et al. |
| 6,736,825 B2 | 5/2004 | Blatter et al. |
| 6,743,244 B2 | 6/2004 | Blatter et al. |
| 6,817,508 B1 | 11/2004 | Racenet |
| 6,821,286 B1 | 11/2004 | Carranza et al. |
| 6,843,403 B2 | 1/2005 | Whitman |
| 6,905,504 B1 | 6/2005 | Vargas |
| 6,942,675 B1 | 9/2005 | Vargas |
| 6,994,669 B1 | 2/2006 | Gannoe et al. |
| 7,025,747 B2 | 4/2006 | Smith |
| 7,055,730 B2 | 6/2006 | Ehrenfels et al. |
| 7,097,089 B2 | 8/2006 | Marczyk |
| 7,111,768 B2 | 9/2006 | Cummins et al. |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,234,624 B2 | 6/2007 | Gresham et al. |
| 7,238,195 B2 | 7/2007 | Viola |
| 7,258,262 B2 | 8/2007 | Mastri et al. |
| 7,401,720 B1 | 7/2008 | Durrani |
| 7,434,715 B2 | 10/2008 | Shelton, IV et al. |
| 7,467,740 B2 | 12/2008 | Shelton, IV et al. |
| 7,497,865 B2 | 3/2009 | Willis et al. |
| 7,506,791 B2 | 3/2009 | Omaits et al. |
| 7,517,356 B2 | 4/2009 | Heinrich |
| 7,588,177 B2 | 9/2009 | Racenet |
| 7,604,151 B2 | 10/2009 | Hess et al. |
| 7,635,073 B2 | 12/2009 | Heinrich |
| 7,635,373 B2 | 12/2009 | Ortiz |
| 7,641,432 B2 | 1/2010 | Lat et al. |
| 7,644,848 B2 | 1/2010 | Swayze et al. |
| 7,673,782 B2 | 3/2010 | Hess et al. |
| 7,735,703 B2 | 6/2010 | Morgan et al. |
| 7,918,873 B2 | 4/2011 | Cummins |
| 2001/0004698 A1 | 6/2001 | Blatter et al. |
| 2001/0023353 A1 | 9/2001 | Vargas et al. |
| 2001/0023354 A1 | 9/2001 | Blatter et al. |
| 2002/0095166 A1 | 7/2002 | Vargas et al. |
| 2003/0014064 A1 | 1/2003 | Blatter |
| 2003/0073981 A1 | 4/2003 | Whitman et al. |
| 2003/0120284 A1 | 6/2003 | Palacios et al. |
| 2003/0236551 A1 | 12/2003 | Peterson |
| 2004/0028502 A1 | 2/2004 | Cummins |
| 2004/0097994 A1 | 5/2004 | Blatter et al. |
| 2004/0225306 A1 | 11/2004 | Blatter et al. |
| 2005/0033329 A1 | 2/2005 | Bombard et al. |
| 2005/0184121 A1 | 8/2005 | Heinrich |
| 2005/0216043 A1 | 9/2005 | Blatter et al. |
| 2005/0267496 A1 | 12/2005 | Loshakove et al. |
| 2005/0267530 A1 | 12/2005 | Cummins |
| 2006/0011699 A1 | 1/2006 | Olson et al. |
| 2006/0041273 A1 | 2/2006 | Ortiz et al. |
| 2006/0151567 A1 | 7/2006 | Roy |
| 2006/0167485 A1 | 7/2006 | Blatter |
| 2006/0241660 A1 | 10/2006 | Bombard et al. |
| 2006/0253143 A1 | 11/2006 | Edoga |
| 2006/0291981 A1 | 12/2006 | Viola et al. |
| 2007/0027472 A1 | 2/2007 | Hiles et al. |
| 2007/0034666 A1 | 2/2007 | Holsten et al. |

| | | |
|---|---|---|
| 2007/0034668 A1 | 2/2007 | Holsten et al. |
| 2007/0073341 A1 | 3/2007 | Smith et al. |
| 2007/0083234 A1 | 4/2007 | Shelton, IV et al. |
| 2007/0118163 A1 | 5/2007 | Boudreaux et al. |
| 2007/0125828 A1 | 6/2007 | Rethy et al. |
| 2007/0175950 A1 | 8/2007 | Shelton, IV et al. |
| 2008/0078807 A1 | 4/2008 | Hess et al. |
| 2008/0172088 A1 | 7/2008 | Smith |
| 2008/0210738 A1 | 9/2008 | Shelton et al. |
| 2008/0272175 A1 | 11/2008 | Holsten et al. |
| 2009/0001128 A1 | 1/2009 | Weisenburgh, II et al. |
| 2009/0005808 A1 | 1/2009 | Hess et al. |
| 2010/0179559 A1 | 7/2010 | Walker |

FOREIGN PATENT DOCUMENTS

| | | |
|---|---|---|
| EP | 1238634 | 9/1994 |
| EP | 1354559 | 5/1995 |
| EP | 1354559 A2 | 5/1995 |
| EP | 0625335 B1 | 11/1997 |
| EP | 0820724 | 1/1998 |
| EP | 0885595 | 12/1998 |
| EP | 0938870 | 9/1999 |
| EP | 0820725 | 1/2000 |
| EP | 0990420 | 4/2000 |
| EP | 1464287 | 10/2004 |
| EP | 1790293 | 5/2007 |
| EP | 1736104 | 3/2009 |
| FR | 2316910 | 7/1976 |
| JP | 2005160933 | 6/2005 |
| RU | 2080833 | 6/1997 |
| SU | 1667844 | 8/1991 |
| WO | WO-81/01953 | 7/1981 |
| WO | WO-85/01427 | 4/1985 |
| WO | WO-98/19625 | 5/1998 |
| WO | WO-99/11178 | 3/1999 |
| WO | WO-99/21491 | 5/1999 |
| WO | WO-00/12013 | 3/2000 |
| WO | WO-00/59380 | 10/2000 |
| WO | WO-2008/042043 | 4/2008 |

OTHER PUBLICATIONS

Ethicon Endo-Surgery, "Atlas of Surgical Stapling", (1999).
"510(k) Notification for the Cardica C-Port Anastomosis System", *Section 9, "Substantial Equivalence," and Appendices B, C, E,* (Unpublished).
Gong, Shao W., "Perfectly flexible mechanism and integrated mechanism system design", *Mechanism and Machine Theory* 39 (2004), (Nov. 2004),1155-1174.
Lim, Jonas J., et al., "A review of mechanism used in laparascopic surgical instruments", *Mechanism and Machine Theory* 38, (2003),1133-1147.
Lim, Jyue B., "Type Synthesis of a Complex Surgical Device", *Masters Thesis*, (Feb. 21, 2001).
Lim, Jonas J., et al., "Application of Type Synthesis Theory to the Redesign of a Complex Surgical Instrument", *Journal of Biomechanical Engineering* (124), (Jun. 2004),265-272.
Kolios, Efrossini et al., "Microlaparoscopy", *J. Endourology* 18(9), (Nov. 2004),811-817.
Steichen, Felicien M., et al., "Mechanical Sutures in Surgery", *Brit. J. Surg.* 60(3), (Mar. 1973),191-197.
"Notification of Transmittal of the International Search Report and the Written Opinion of the International Searching Authority", PCT/US2008/075449, (Apr. 29, 2009).
"International Search Report", PCT/US2008/075449, (Apr. 29, 2009).
"Written Opinion of the International Searching Authority", PCT/US2008/075449, (Apr. 29, 2009).
"Cardica Microcutter Implant Delivery Device 510(k), Cover Sheet, Table 10.1, "Substantial Equivalence Comparison," and Section 12, "Substantial Equivalence Discussion"".
"European Search Report, EP08829324".
"Transmittal of European Search Report, EP08829324".
"European Search Opinion, EP08829324".
"China—First Office Action", CN 200880106148.6, Jun. 24, 2011.
"Office Action (Japan)", (Feb. 28, 2012).

* cited by examiner

TRUE MULTI-FIRE ENDOCUTTER

This patent application is a continuation of U.S. patent application Ser. No. 11/851,379 filed on Sep. 6, 2007, which is herein incorporated by reference in its entirety.

FIELD OF THE INVENTION

The invention generally relates to a surgical tool and method, and more specifically to an endocutter.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The surgeon inserts the endocutter through a trocar or other port or incision in the body, orients the end of the endocutter around the tissue to be transected, and compresses the anvil and cartridge together to clamp the tissue. Then, a row or rows of staples are deployed on either side of the transection line, and a blade is advanced along the transection line to divide the tissue.

During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter. That inconvenience may discourage surgeons from using the endocutter for procedures in which use of an endocutter may benefit the patient.

BRIEF DESCRIPTION OF THE DRAWINGS

FIG. 17A is a perspective view of the underside of the retainer of FIG. 17.

The use of the same reference symbols in different figures indicates similar or identical items.

DETAILED DESCRIPTION

Endocutter—Three Staple Rows

Figure 1:
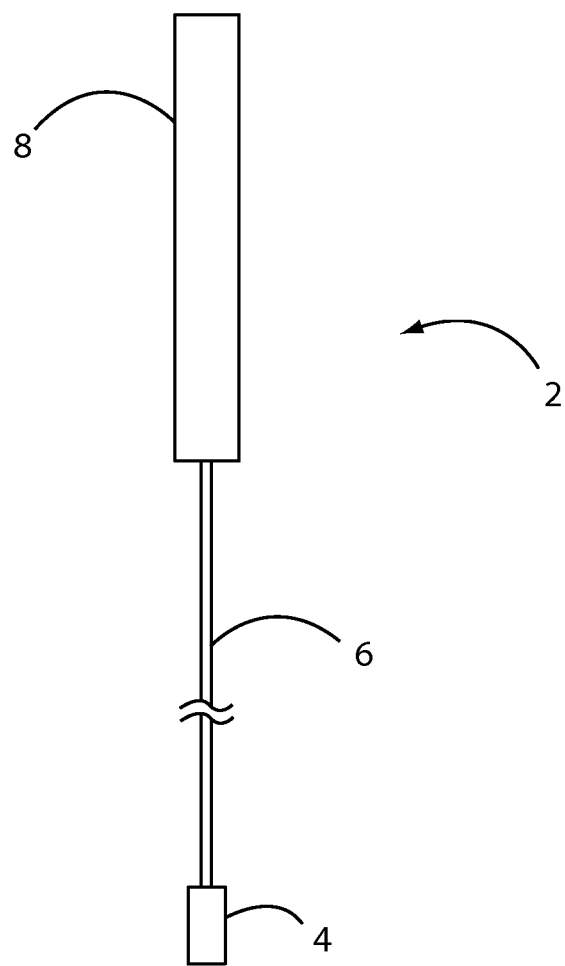
FIG. 1 is a schematic view of an endocutter.
Figure 2:
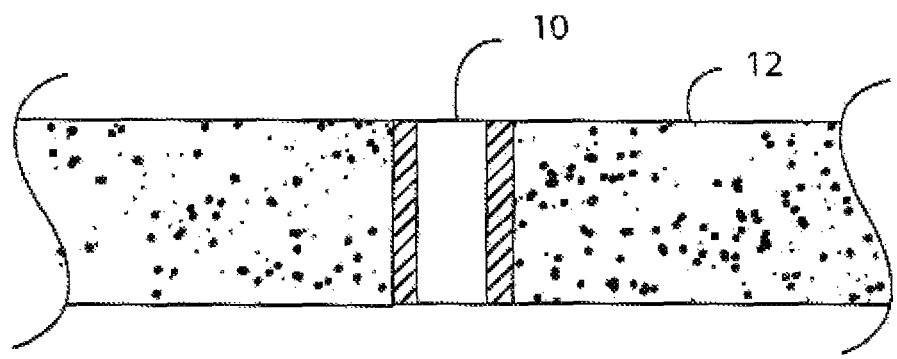
FIG. 2 is a cross-section view of a trocar port positioned in a patient.
Figure 3:
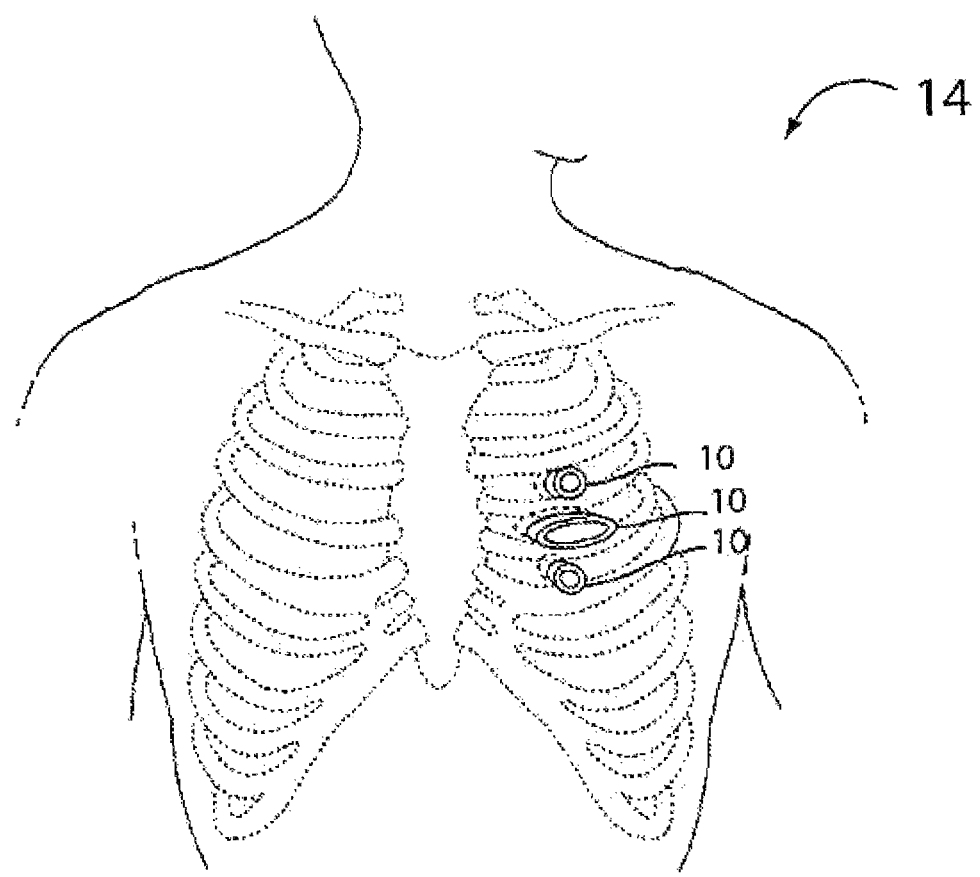
FIG. 3 is a cross-section view of trocar ports positioned in a patient.

Referring to FIG. 1, an endocutter 2 includes an end effector 4 attached to a shaft 6, which in turn is attached to a handle 8. The end effector 4 may be one or more separate components that are connected to the shaft 6, or may be fabricated integrally with the distal end of the shaft 6. Referring also to FIGS. 2-3, the end effector 4 and the shaft 6 may be sized to pass through a standard trocar port 10 that may be placed through tissue 12 of a patient 14. Advantageously, the end effector 4 may be sized to pass through a trocar port 10 having an opening between 5-10 millimeters in diameter. Alternately, the endocutter 2 may be used in the course of conventional open surgery, where a trocar port is not used. Alternately, the endocutter 2 may be used in the course of minimally-invasive surgery, where access to the surgical site in the patient is gained through a mechanism or structure other than a trocar port, such as the LAP DISC® hand access device of Ethicon Endo-Surgery, Inc., or where access to the surgical site in the patient is gained through an incision or opening in which no port or other mechanism or structure is placed.

The trocar port 10 is a hollow generally-tubular structure inserted into an incision in tissue 12 of a patient to hold that incision open and to prevent damage to the tissue 12 defining the incision opening that may result from the motion of tools and other objects through the incision. The trocar port 10 may be made from plastic or any other suitable biocompatible material. The trocar port 10 may have a substantially circular cross section, a substantially oval cross section, or any other suitable cross section. The particular dimensions of a trocar port 10 depend on the particular procedure to be performed on the patient 14, and may be any suitable dimensions. The trocar port 10 may be coupled to a cutting tool (not shown) through its center that makes an opening in tissue 12, after which the trocar port 10 is placed into tissue 12. The cutting tool may be a spike or other cutting or puncturing device, which is removed from the trocar port 10 when the trocar port 10 is in position in the chest wall. The combination of a trocar port 10 and a cutting tool is standard in the art.

Referring to FIG. 1, the shaft 6 of the endocutter 2 extends proximally from the end effector 4. The shaft 6 may be flexible or rigid. The shaft 6 may be articulated in at least one location, if desired. Optionally, the shaft 6 may include a cutaway, trough or other feature (not shown) to allow a guidewire (if any) or other positioning aid that may be used in the surgical procedure to remain in place during actuation of the endocutter 2.

The handle 8 may be attached to the proximal end of the shaft 6, or any other suitable portion of the shaft 6. The shaft 6 may be fabricated integrally with the handle 8. Alternately, the shaft 6 and the handle 8 may be two separate items that are connected together in any suitable manner. The handle 8 may include any mechanism, mechanisms, structure or structures that are suitably configured to actuate the end effector 4. The handle 8 may also include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in the U.S. patent application Ser. No. 11/054,265, filed on Feb. 9, 2005, which is herein incorporated by reference in its entirety. The handle 8 may instead, or also, include a connector or connectors suitable for receiving stored energy from an external source, such as a hose connected to a hospital utility source of pressurized gas or of vacuum, or an electrical cord connectable to a power source.

Figure 4:
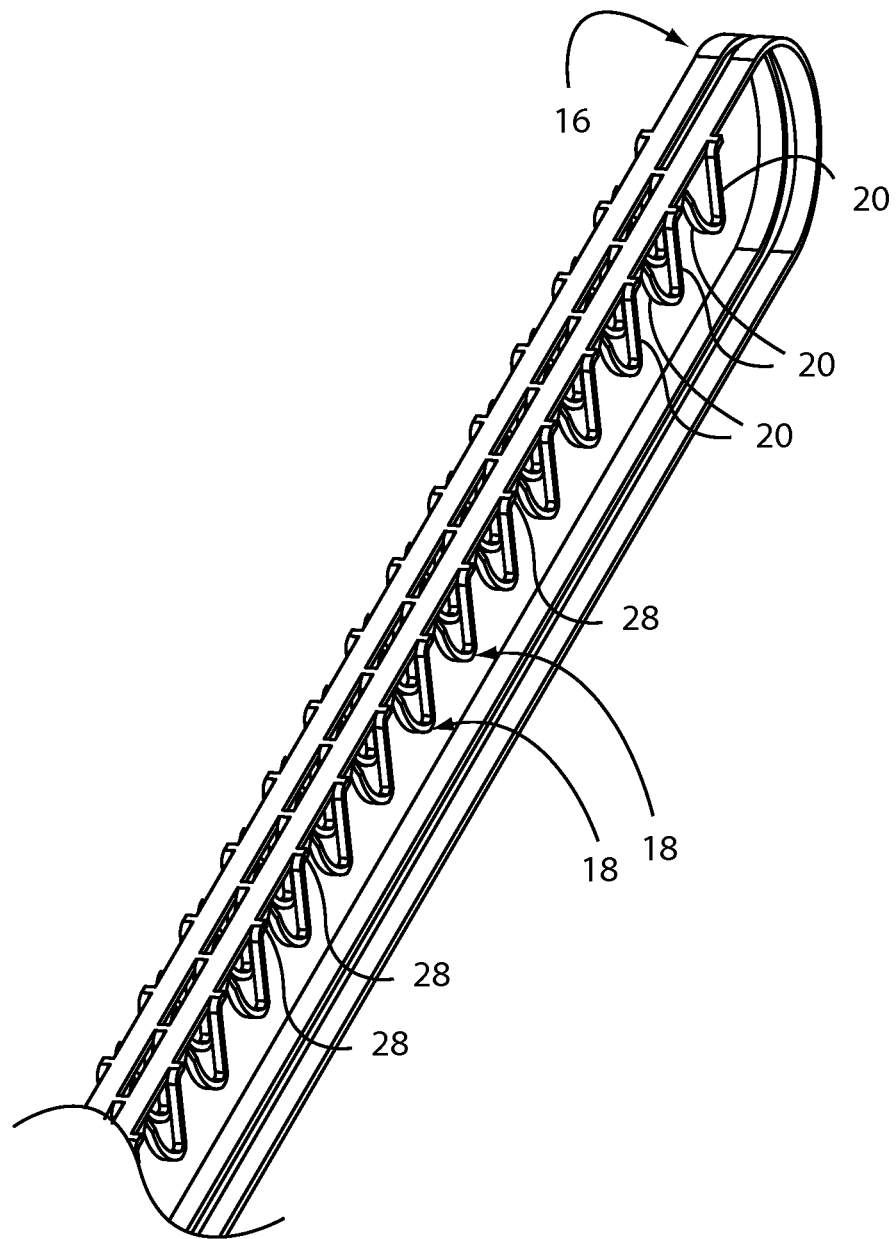
FIG. 4 is a perspective view of an exemplary feeder belt with three rows of staples frangibly connected thereto.
Figure 5:
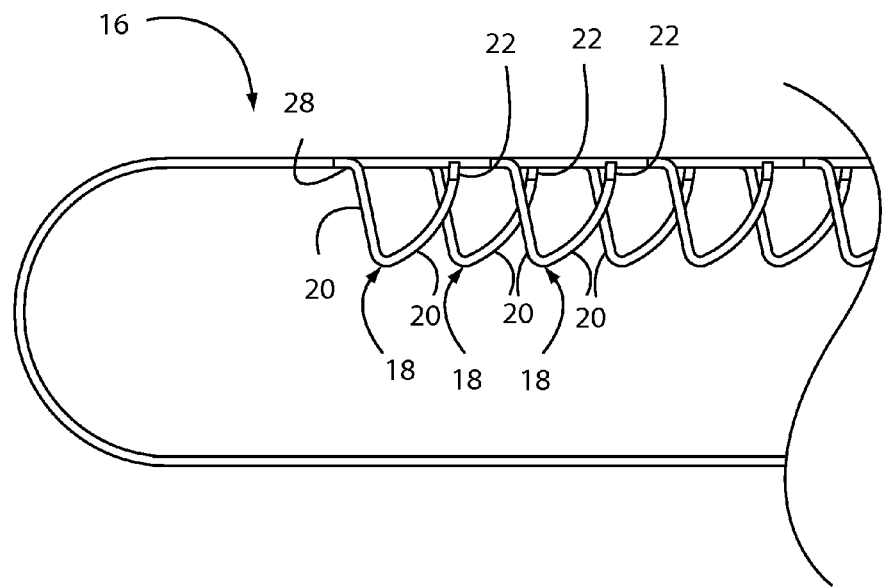
FIG. 5 is a side view of the feeder belt of FIG. 4.
Figure 6:
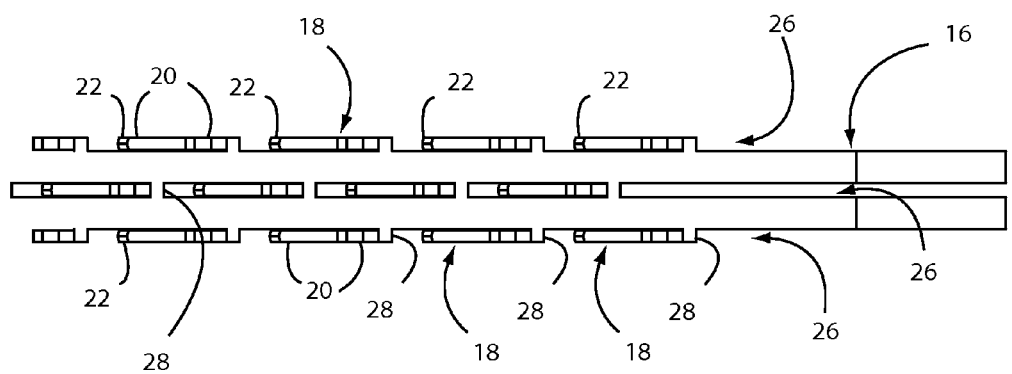
FIG. 6 is a top view of the feeder belt of FIG. 4.

Referring to FIGS. 4-6, a portion of a feeder belt 16 is positioned within the end effector 4. The feeder belt 16 may be a long, narrow, thin strip of material from which one or more staples 18 extend. The feeder belt 16 may be fabricated from stainless steel, nickel-titanium alloy, or any other suitable metallic or non-metallic material. The feeder belt 16 is flexible enough, and strong enough, to be advanced linearly and then redirected around a nose or other structure in substantially the opposite direction, as described in greater detail below. Alternately, the feeder belt 16 may be rigid or at least partially rigid, and may be advanced or retracted substantially linearly without redirection about a structure. Each staple 18 may be shaped in any suitable manner; the staples 18 may be shaped substantially the same as one another, or may be shaped differently. As one example, each staple 18 is generally V-shaped, and has two legs 20 extending from the base of the V-shape. Referring particularly to FIG. 5, one leg 20 of the staple 18 may be generally straight, and the other leg 20 of the staple 18 may be gently curved. However, the legs 20 may be shaped in a different manner. Further, each leg 20 may be shaped in the same manner. The staple 18 need not be symmetrical, but can be fabricated symmetrically if desired. The base of the V-shape of the staple 18 may be curved, pointed or otherwise configured. One leg 20 of the staple 18 has a free end 22 that may be characterized as a tissue penetrating tip 22. The tissue penetrating tip 22 may be sharpened, if desired, to facilitate penetration of tissue. However, the legs 20 of the staple 18 may have a cross-section that is small enough that the tissue penetrating tip 22 need not be sharpened in order to easily penetrate tissue. The other leg 20 is attached at one end to the feeder belt 16. Advantageously, that leg 20 is frangibly connected to the feeder belt 16. Thus, one end of the staple 18 may be attached to the feeder belt 16 and the other end of the staple 18 may be free. Alternately, the staple 18 may have three or more legs 20, or may be shaped in any other suitable manner.

The feeder belt 16 and staples 18 may be fabricated in any suitable manner. As one example, a flat, thin sheet of material is laser cut into long strips, after which each strip is laser cut to form fingers therein that are then bent into the shape of the staples 18. In this way, the staples 18 and the feeder belt 16 form an integral structure. However, the feeder belt 16 and staples 18 may be fabricated in any other suitable manner. As one example, the staples 18 and feeder belt are fabricated separately, and the staples 18 are then connected to the feeder belt 16 by welding, adhesive, or any other method that provides a frangible connection between the staples 18 and the feeder belt 16.

A frangible connection between the feeder belt 16 and each corresponding staple 18 may be made in any suitable manner. As one example, referring particularly to FIG. 6, each feeder belt 16 may include at least one tab 28 protruding laterally therefrom, or defined laterally in the center thereof. Alternately, at least one tab 28 may be oriented differently. Advantageously, the tabs 28 result from laser cutting and subsequent mechanical deformation of the staples 18 during manufacturing, such that the tabs 28 and staples 18 are integral with the corresponding feeder belt 16. However, the tabs 28 and/or staples 18 may be fabricated and connected to the feeder belt 16 in any other suitable manner. At least one staple 18 may be attached to a corresponding tab 28 in any suitable manner. The attachment between a staple 18 and the corresponding tab 28 may be made in any suitable manner, and the connection between a staple 18 and the corresponding tab 28 may have any suitable orientation. As one example, at least one tab 28 is generally rectangular, and the corresponding staple 18 extends from the proximal edge of that rectangular tab 28. The staple 18 may be separable from the tab 28, at a location generally at the intersection between the staple 18 and the tab 28. The connection between a staple 18 and the corresponding tab 28 is strong enough to hold the staple 18 securely in place relative to the feeder belt 16 prior to deployment, and weak enough to be broken or otherwise separated from the tab 28 during or after deployment. Optionally, a staple 18 and/or tab 28 may include a weakened area at or near their intersection, in order to facilitate separation between the staple 18 and the feeder belt 16 during or after deployment. The weakened area may have a reduced cross-sectional area, may be notched, or otherwise structurally weakened. Alternately, the weakened area may also, or instead, be physically treated or otherwise configured to be weaker than the surrounding material, while having substantially the same physical dimensions as that surrounding material.

As shown in FIGS. 4-6, the staples 18 are in an initial configuration prior to being deployed. In the initial configuration, the staples 18 do not substantially contact one another. Alternately, at least two of the staples 18 may contact one another in the initial configuration. The staples 18 each may lie substantially in a single plane. That is, the staple 18 may be shaped such that a single plane extends through and substantially bisects the staple 18. Alternately, at least one staple 18 does not lie substantially in a single plane. At least one staple 18 may be positioned in a plane that is generally perpendicular to the feeder belt 16. Alternately, at least one staple 18 may be positioned in a plane that is angled differently relative to the feeder belt 16. One or more rows 26 of staples 18 are connected to the feeder belt 16. Each row 26 of staples 18 is the group of staples 18 positioned at substantially the same lateral location relative to the longitudinal centerline of the feeder belt 16, and each row 26 of staples 18 is oriented generally longitudinally. As best seen in FIG. 6, three rows 26 of staples 18 may be attached to the feeder belt 16—one row 26 along each side of the feeder belt 16, and one row 26 along the center of the feeder belt 16. The feeder belt 16 may form a continuous loop, or may have a discrete beginning and end that are not attached to one another. Alternately, more or fewer rows 26 of staples 18 may be attached to the feeder belt 16. Each row 26 may extend along part, or all, or the length of the feeder belt 16. Different rows 26 may extend different lengths along the feeder belt 16.

Staples 18 in two or more different rows 26 along a single feeder belt 16 may be arranged in any suitable manner relative to one another. As one example, staples 18 in two or more different rows 26 along a single feeder belt 16 may be staggered relative to one another. That is, at a given longitudinal position along a single feeder belt 16 at which a staple 18 in one row 26 is attached to the feeder belt 16, at least one other row 26 does not have a staple 18 attached to that feeder belt 16. This staggering of the staples 18 promotes hemostasis in tissue treated with the end effector 4. As may be best seen in FIG. 6, the center row 26 of staples 18 may be staggered relative to the rows 26 of staples 18 along the lateral edges of the feeder belt 16. Alternately, two or more rows 26 of staples 18 may be staggered in a different manner. Alternately, staples 18 in two or more of the rows 26 along a single feeder belt 16 may be aligned with one another, along at least part of the length of the rows 26, such that at a given longitudinal position along the feeder belt 16 at which a staple 18 in one row 26 is attached to the feeder belt 16, each other row 26 has a staple 18 attached to the feeder belt 16 as well. Alternately, staples 18 in two or more rows 26 along a single feeder belt 16 may be arranged differently along different longitudinal portions of that feeder belt 16. Staples 18 may be arranged relative to one another in the same manner, or differently, on different feeder belts 16 of the endocutter 2.

The staples 18 in each row 26 may be substantially evenly spaced apart from one another. That is, the distance between any two longitudinally-adjacent staples 18 in a row may be substantially the same. Alternately, at least two longitudinally-adjacent staples 18 in each row 26 may be spaced apart a distance different from the distance between two other longitudinally-adjacent staples 18. Such a configuration may be useful where the length of the staple line is not adjustable. The staple line to be created with the end effector 4 may be fixed at a particular number of staples 18, and consequently the staples 18 in each row may be grouped together in groups each having a length substantially the same as that fixed staple line. If so, each group of staples 18 in a row 26 may be separated from a adjacent group of staples 18 by a blank space on the feeder belt 16, where that blank space may have any suitable length. Advantageously, no staples 18 extend from, or into an area bounded by, the blank space of the feeder belt 16.

Figure 7:
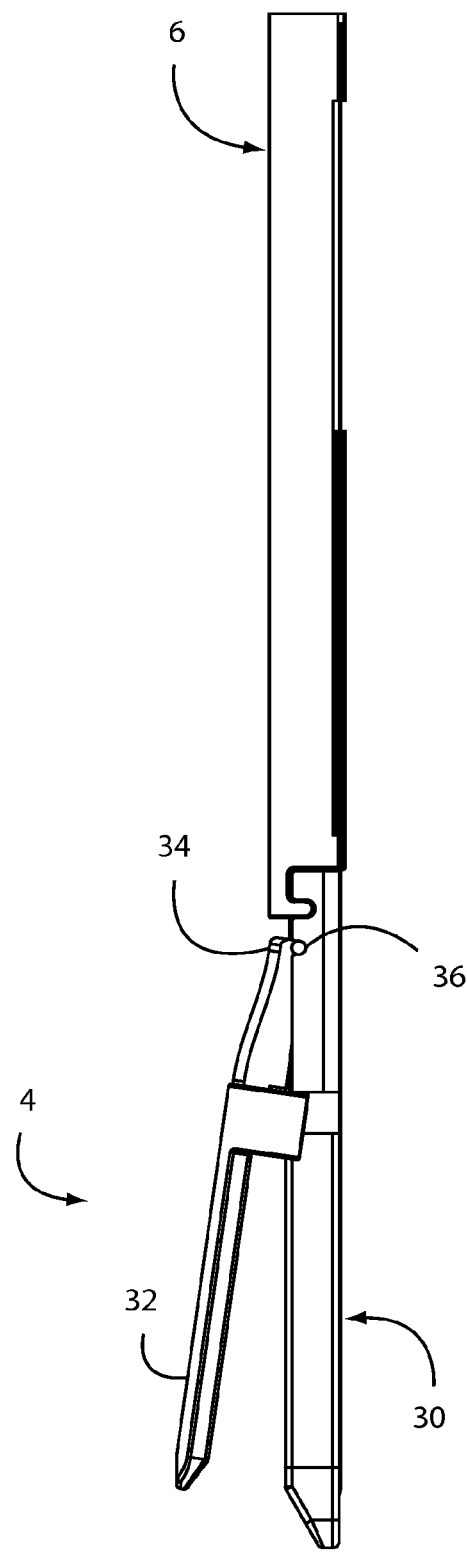
FIG. 7 is a side view of an exemplary end effector of an endocutter that utilizes the feeder belt of FIGS. 4-6.
Figure 16:
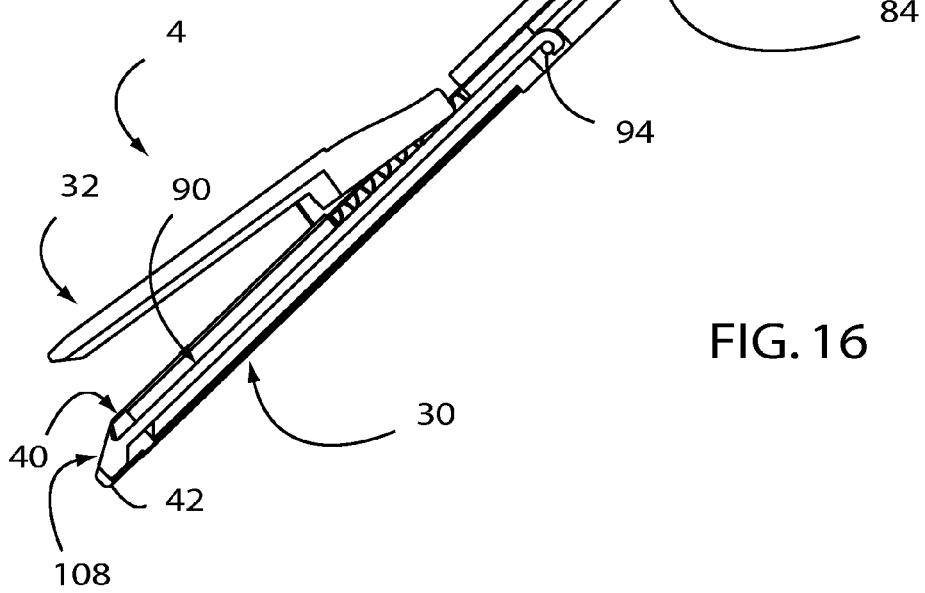
FIG. 16 is a side cutaway view of the exemplary end effector of FIG. 7.

Referring also to FIG. 7, the end effector 4 may include a staple holder 30 and an anvil 32. The anvil 32 may be movable relative to the staple holder 30 to compress tissue therebetween. The anvil 32 may include standard staple bending features defined therein to facilitate closure of the staples 18. Alternately, staple bending features may be omitted from the anvil 32. The anvil 32 may be pivotable relative to the staple holder 30. As one example, at least one pin 34 may extend generally laterally from the anvil 32 at a location at or near the proximal end of the anvil 32. Each pin 34 may be received by a trough 36, aperture, or other feature of the staple holder 30 that allows that pin 34 to rotate therein and thereby allows the anvil 32 to pivot. Referring also to FIG. 16, in this way, the distal end of the anvil 32 may be spaced apart from and positioned above the staple holder 30 in a first, initial position prior to clamping tissue, while the proximal end of the anvil 32 may be connected to the staple holder 30. Alternately, the trough 36 may be located in the shaft 6 of the endocutter, such that the anvil 32 is pivotally attached to the shaft 6 and movable relative to the staple holder 30. Alternately, the anvil 32 may be connected to and/or movable relative to the staple holder in a different manner. Alternately, the staple holder 30 may be movable relative to the anvil 32. Alternately, the staple holder 30 and the anvil 32 may be movable relative to one another. The distal end of the staple holder 30 and the distal end of the anvil 32 may be blunt, in order to prevent inadvertent engagement of tissue with the end effector 4 during insertion of the end effector 4 into the patient and motion of the end effector 4 to a treatment site. Advantageously, the staple holder 30 is fixed to a remainder of the end effector 4 and/or the shaft 6, and is not detachable therefrom. As set forth in greater detail below, the staple holder 30 may be fired multiple times without being withdrawn from the patient, such that there is no need to withdraw the end effector 4 from the patient after each firing of staples 18 in order to replace a staple cartridge or other component. Nevertheless, if desired the staple holder 30 may be detachable from a remainder of the end effector 4 and/or the shaft 6; the end effector 4 may be detachable from the shaft 6; and/or the shaft 6 may be detachable from the handle 8.

Figure 8:
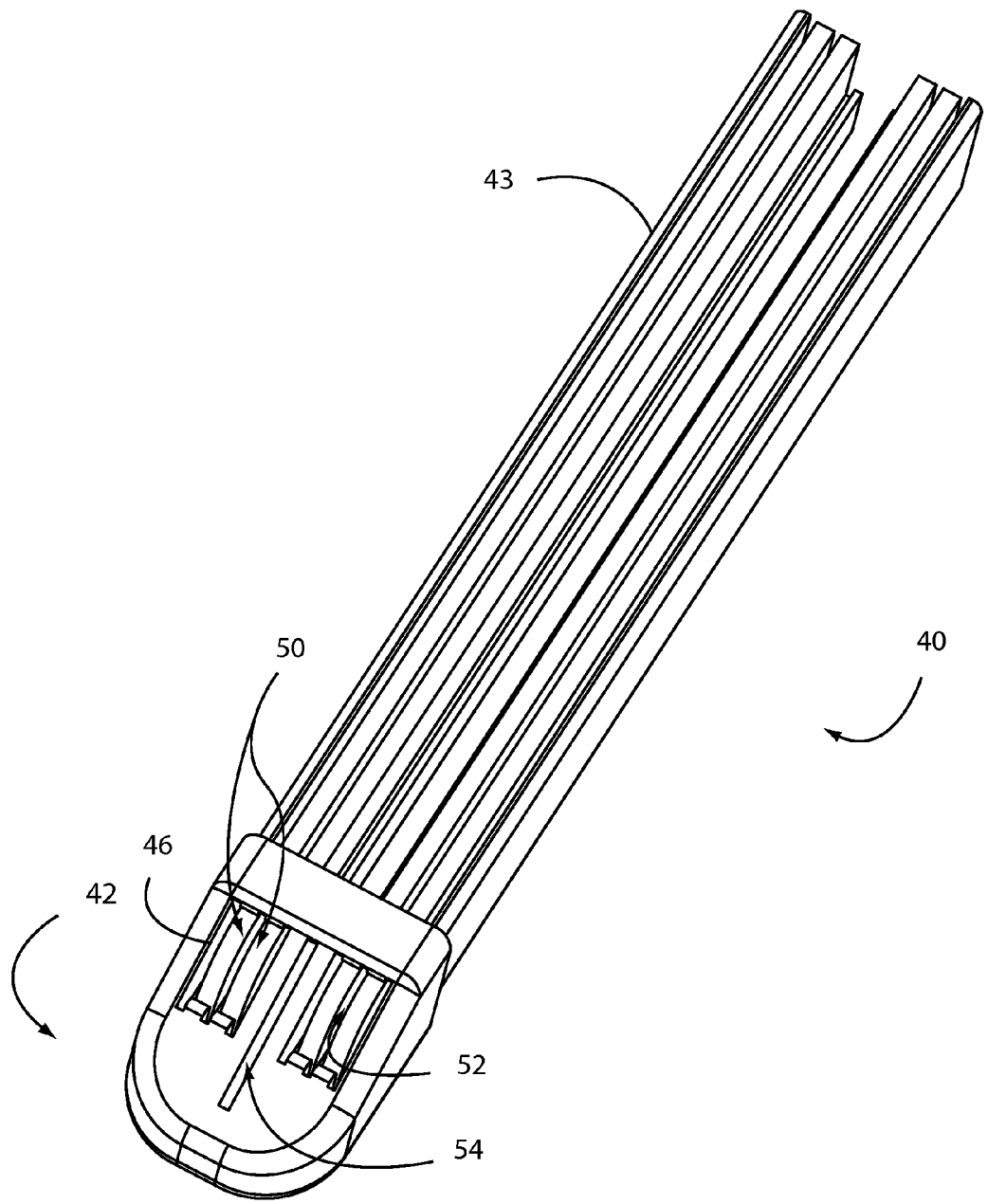
FIG. 8 is a perspective view of an exemplary feeder belt guide.
Figure 9:
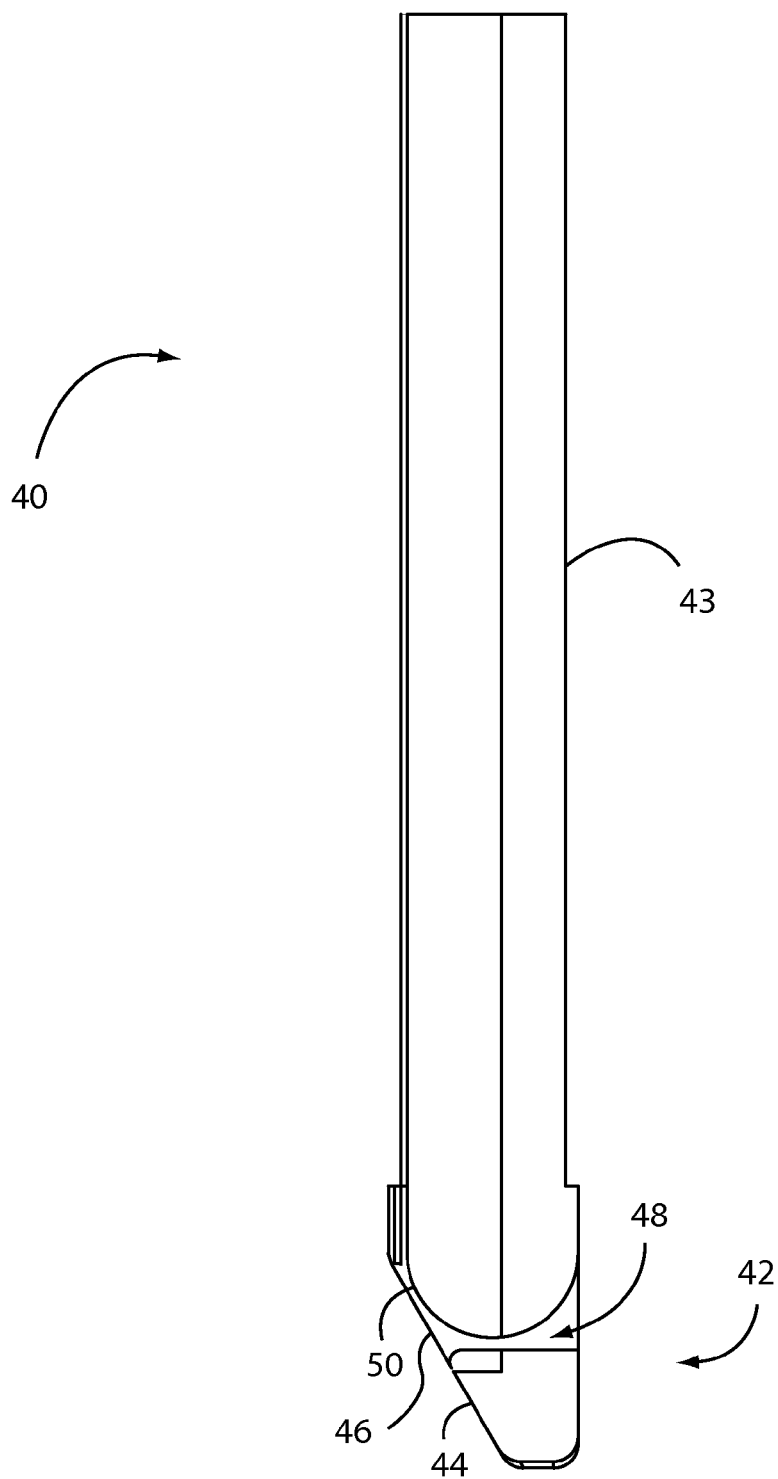
FIG. 9 is a side cross-section view of the feeder belt guide of FIG. 8, not including a feeder belt.
Figure 10:
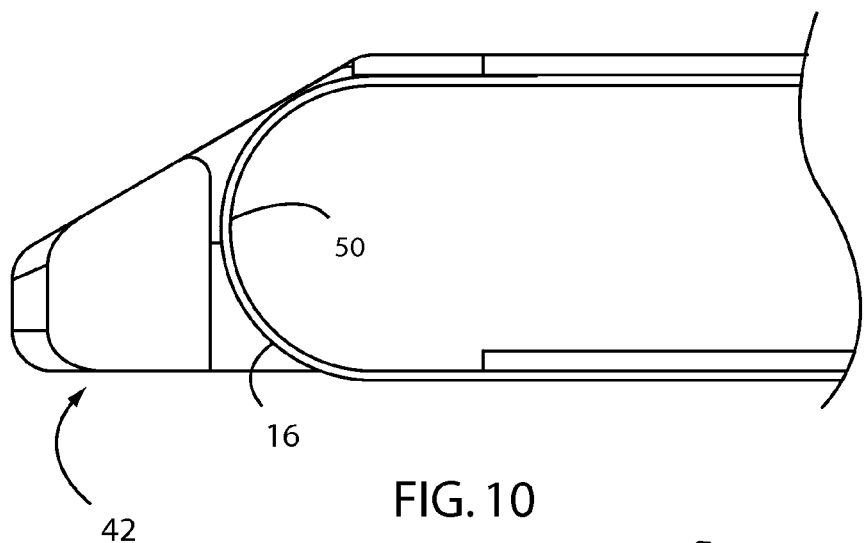
FIG. 10 is a side cross-section view of the feeder belt guide of FIG. 8, including a feeder belt.

The staple holder 30 may include any suitable components. Referring also to FIGS. 8-10, the staple holder 30 may include a feeder belt guide 40. The feeder belt guide 40 may be shaped in any suitable manner. The staple holder 30 may be configured such that the distal end of the feeder belt guide 40 is the distal end of the end effector 4. If so, the distal end 42 of the feeder belt guide 40 may be generally blunt. The upper surface 44 of the distal end 42 of the feeder belt guide 40 may be angled generally upward, moving proximally along the feeder belt guide 40. Alternately, the upper surface 44 of the distal end 42 of the feeder belt guide 40 may be shaped in any other suitable manner One or more apertures 46 may be defined in the upper surface 44 of the distal end 42 of the feeder belt guide 40. Alternately, one or more of the apertures 46 may be omitted, such that the upper surface 44 of the distal end 42 of the feeder belt guide 40 is instead continuous. The distal end 42 of the feeder belt guide 40 may include a space 48 defined therein. At least one nose 50 may protrude distally into that space 48. Each nose 50 may be curved, and may have a convex shape. As one example, each nose 50 may have an arcuate shape, where that arc is a section of a circle. Alternately, at least one nose 50 may be shaped differently. As one example, at least one nose 50 may be shaped as two or more straight lines that collectively approximate a curve, roughly or smoothly.

Figure 12:
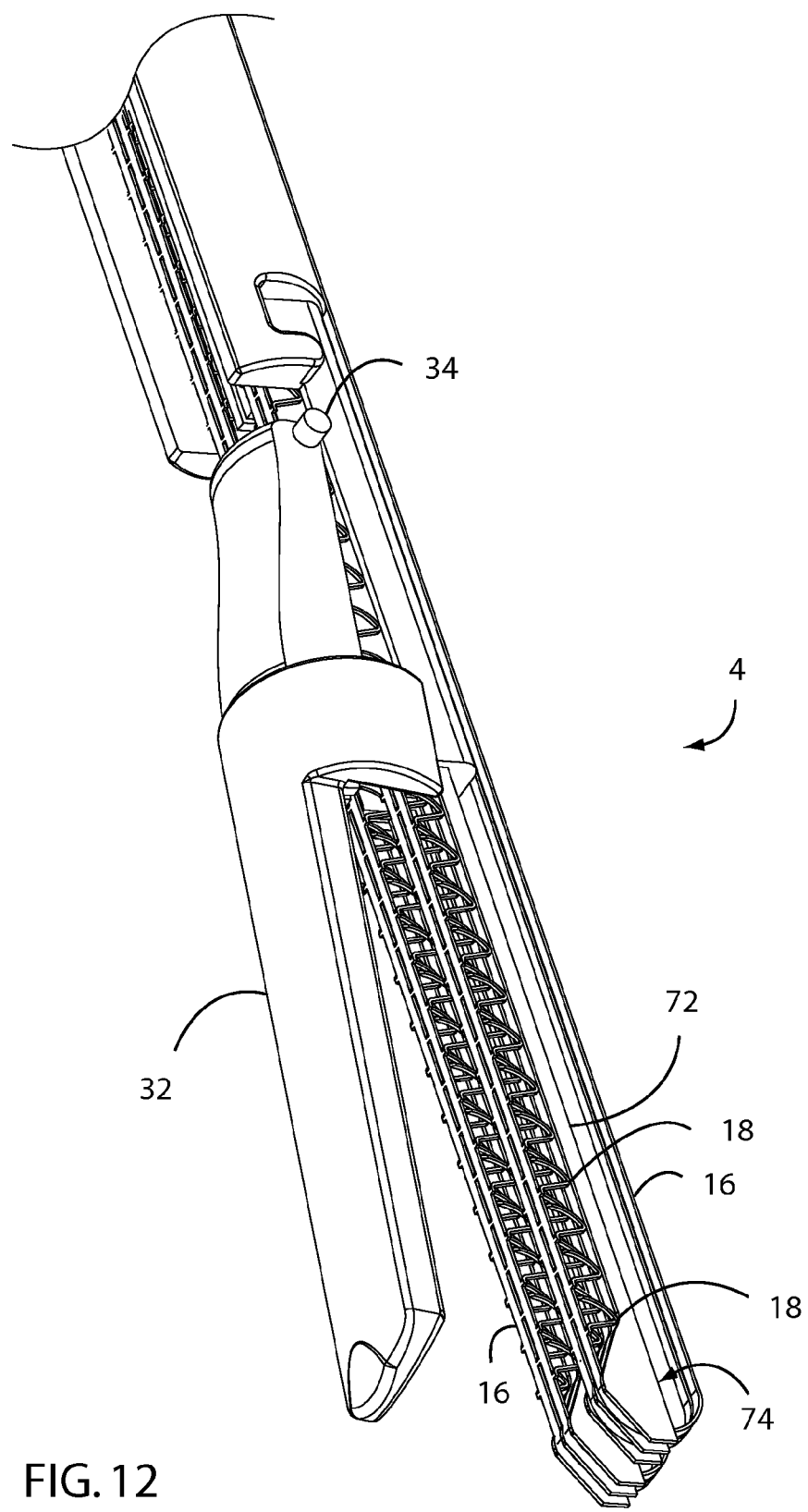
FIG. 12 is a perspective cutaway view of the exemplary end effector of FIG. 7.

Referring also to FIG. 12, the end effector 4 may include two feeder belts 16. In this way, staples 18 can be deployed on either side of an incision or transection to be made in tissue. Alternately, the end effector 4 may include only one feeder belt 16, or three or more feeder belts 16. The feeder belts 16 may be independent of one another, or connected to one another in any suitable manner. A feeder belt 16 may be routed around each nose 50, where the noses 50 are laterally spaced from one another and positioned on opposite sides of a knife, which is described below. Each feeder belt 16 may be routed along a path that starts generally straight and in the distal direction, then is curved along the surface of the corresponding nose 50, and then is generally straight and in the proximal direction. That is, the nose 50 changes the direction of motion of the corresponding feeder belt 16 from generally distal to generally proximal. Each nose 50 may be substantially as wide as the corresponding feeder belt 16 that moves along its surface. Alternately, at least one nose 50 may be narrower than, or wider than, the corresponding feeder belt 16. Alternately, the nose 50 may be omitted, where the feeder belt 16 is movable generally linearly.

At least one nose 50 may be bifurcated by a slot 52 defined therein. The slot 52 may be oriented generally longitudinally. However, the slot 52 may be defined in any other suitable orientation. Each feeder belt 16 is positioned in contact with at least part of a corresponding nose 50, with staples 18 in each lateralmost row 26 of the feeder belt 16 positioned laterally on either side of the nose 50. Where the feeder belt 16 includes a row 26 of staples 18 in the middle of that feeder belt, such as shown in FIG. 6, the slot 52 in the nose 50 may be laterally oriented in substantially the same position as the middle row 26 of staples 18. In this way, the slot 52 provides space for that middle row 26 of staples 18 to slide along. Alternatively, at least one nose 50 may be divided into segments by two or more slots 52, depending on the number of rows 26 of staples 18 attached to the corresponding feeder belt 16. Alternatively, the slot or slots 52 need not extend to the distal end of the nose 50, because the staples 18 have been deployed from the corresponding segment of the feeder belt 16 by the time that segment of the feeder belt 16 reaches the nose 50, as described in greater detail below. Alternately, at least one slot 52 may be omitted. At least one nose 50 may extend in the proximal direction any suitable length. Similarly, the remainder of the feeder belt guide 40 may extend in the proximal direction any suitable length. The portion of the feeder belt guide 40 proximal to the distal end 42 may be referred to as the insert 43. A knife slot 54 may extend along the length of the feeder belt guide 40, and may extend through the upper surface 44 of the distal end 42 of the feeder belt guide 40.

Figure 11:
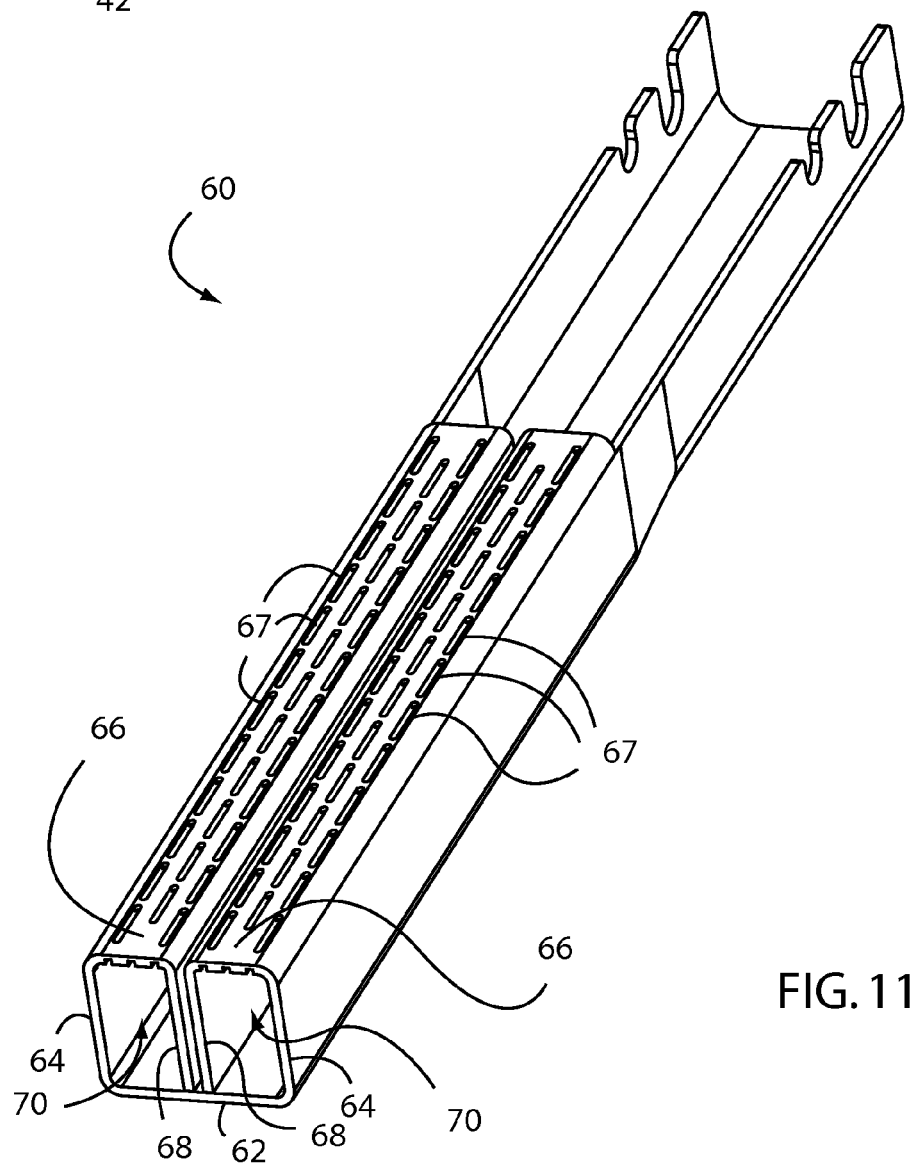
FIG. 11 is a perspective view of an exemplary housing of a staple holder of the exemplary end effector of FIG. 7.

Referring to FIG. 11, a housing 60 is shown. The housing 60 may be fabricated from a single piece of sheet metal. Alternately, the housing 60 may be fabricated in any other suitable manner and/or from any other material. The housing 60 may include a generally flat base 62, with two outer walls 64 extending upward generally perpendicularly from the base 62. The base 62 and outer walls 64 may be generally rectangular. The outer walls 64 may be generally parallel to one another. Alternately, the base 62 and outer walls 64 may be shaped differently, and/or oriented differently relative to one another. A top plate 66 may extend generally laterally from the upper edge of each outer wall 64, such that the two top plates 66 generally lie in the same plane. Each top plate 66 may be generally rectangular. A number of apertures 67 may be defined in each top plate 66, where the apertures 67 allow for deployment of staples 18 therethrough. The two top plates 66 may be spaced apart from one another along their length. An inner wall 68 extends generally downward from the inner edge of each top plate 66, and may be generally perpendicular to the corresponding top plate 66. Each inner wall 68 may be generally rectangular, and the inner walls 68 may be spaced apart from and generally parallel to one another. However, at least one inner wall 68 may be shaped and/or oriented differently. The inner walls 68 may be spaced apart far enough to allow a knife to pass between them, as described in greater detail below. The lower edge of at least one inner wall 68 may contact the base 62, or may be spaced apart from the base 62. A receiving space 70 is a volume in the housing created by the base 62, outer wall 64, top plate 66 and inner wall 68. Two receiving spaces 70 may be defined in the housing 60.

At least part of the housing 60 may omit the top plates 66 and/or inner walls 68, such that at least part of the housing 60 is generally U-shaped. The feeder belt guide 40 may be attached to the housing 60. This attachment may be accomplished in any suitable manner. As one example, the insert 43 portion of the feeder belt guide 40 may be inserted into one or more receiving spaces 70, then fixed thereto in any suitable manner. As another example, the feeder belt guide 40 may not include an insert 43, and the feeder belt guide is attached to the distal end of the housing 60 in any suitable manner. As another example, the feeder belt guide 40 may be fabricated integrally with the housing 60. Alternately, the feeder belt guide 40 is not attached to or fixed to the housing 60.

Figure 13:
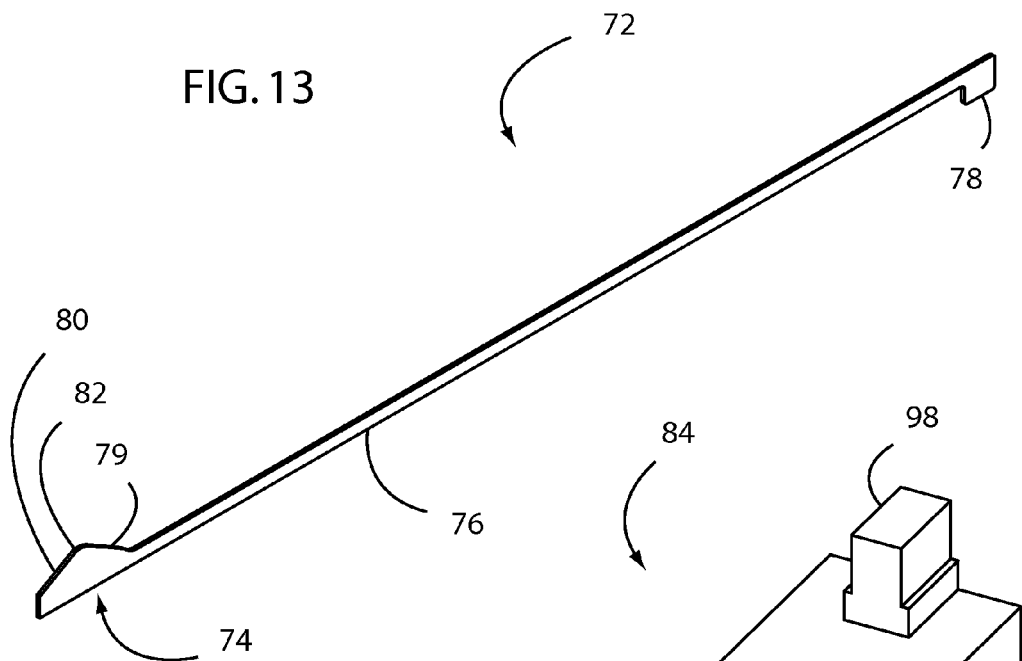
FIG. 13 is a perspective view of an exemplary wedge assembly.

Referring also to FIG. 13, one or more wedge assemblies 72 extend into the staple holder 30 of the end effector 4. Each wedge assembly 72 may include a wedge 74 at the distal end of a arm 76. Alternately, the wedge 74 may be positioned at a different location on the arm 76. The wedge 74 may be shaped in any suitable manner. As one example, the upper surface of the wedge 74 may include a first surface 79 that may be angled or curved upward, moving in the distal direction. The wedge 74 may also include a second surface 80 distal to the first surface 79, where the second surface may be angled or curved downward, moving in the distal direction. The intersection between the first surface 79 and the second surface 80 may be a curved or smooth peak 82. Alternately, the peak 82 may form an unsmoothed angle between the first surface 79 and the second surface 80. The lower surface of the wedge 74 may be substantially linear. Alternately, the lower surface of the wedge 74 may be curved, angled or otherwise shaped in any suitable manner. A tab 78 may be connected to the proximal end of the arm 76. Alternately, the tab 78 may be positioned at a different location on the arm 76. The tab 78 may be substantially rectangular, or may be shaped in a different manner. The tab 78 may extend in a downward direction from the arm 76, and the wedge 74 may extend in an upward direction from the arm 76. Alternately, the wedge 74 and/or tab 78 are oriented differently relative to the arm 76. Advantageously, the wedge assembly 72 is fabricated as a single, integral structure. However, the wedge assembly 72 may be assembled from separate components, in any suitable manner. Referring to FIG. 12, each wedge 74 may be initially positioned distal to a row 26 of staples 18, and may be generally longitudinally aligned with, and longitudinally movable relative to, that corresponding row 26 of staples 18. The length of each wedge 74 may be equal to or less than the longitudinal spacing between staples 18 in a row 26, such that the wedge 74 deploys each staple 18 before moving into contact with the subsequent staple 18 in the row 26. This configuration of wedge 74 is particularly useful where the length of the staple line is adjustable, because the deployment of one staple 18 is independent of the deployment of any other staple 18. Alternately, the wedge 74 may be longer than the longitudinal spacing between staples 18 in a row 26, such that deployment of one staple 18 concludes while the longitudinally-adjacent staple 18 is in the middle of deployment. Such a configuration of wedge 74 may be useful where the length of the staple line is fixed, and a blank space is provided on the feeder belt 16 between groups of staples 18 along a row 26.

Figure 14:
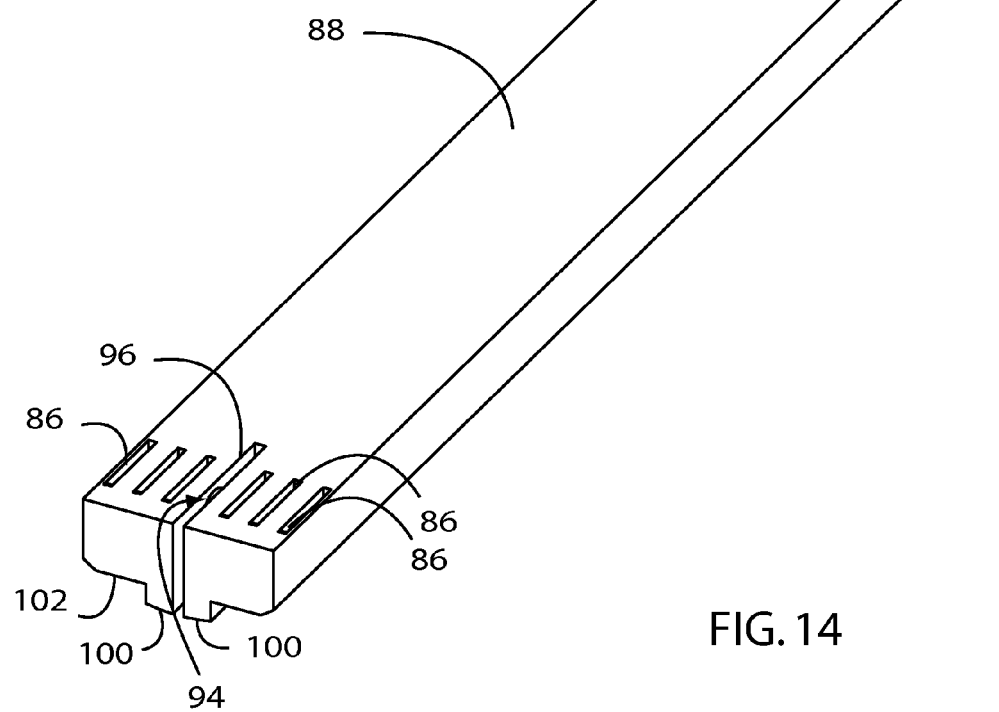
FIG. 14 is a perspective view of an exemplary block of the exemplary end effector of FIG. 7.
Figure 15:
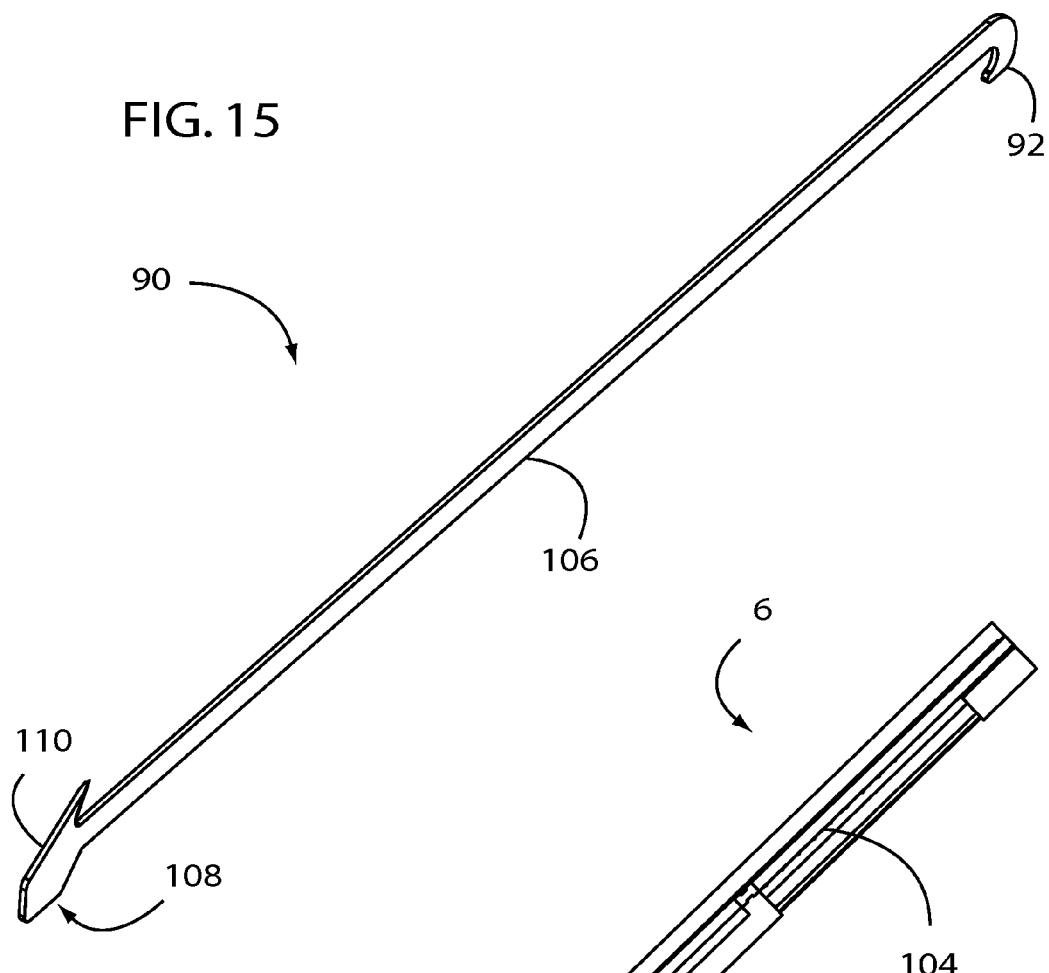
FIG. 15 is a perspective view of an exemplary cutter.

Referring also to FIG. 14, the tab 78 of each wedge assembly 72 may be inserted into a receiving slot 86 in a block 84. Each receiving slot 86 may be defined partially into, or completely through, the block 84. The receiving slot or slots 86 may be defined in the upper surface 88 of the block 84, or in a different surface of the block 84. The receiving slot or slots 86 may be positioned at or near the distal end of the block 84, or at a different location on the block 84. Referring also to FIG. 15, a knife 90 may include a hook 92 at its proximal end. A pin 94 may extend laterally across a knife receiving slot 96 defined in the distal end of the block 84, and the hook 92 may engage that pin 94. The pin 94 may be generally cylindrical, or may have any other suitable shape for engaging the hook. Alternately, the knife receiving slot 96 is defined in a different part of the block 84. Alternately, the hook 92 of the knife 90 may be a tab similar to the tab 78 of the wedge assembly 72, and the knife receiving slot 96 may thus be configured in the same way as the receiving slots 86 for the tabs 78 of the wedge assemblies 72. Alternately, the hook 92 may be shaped in any other suitable manner, such as a shape that is not a hook, and the knife receiving slot 96 may be configured accordingly. Alternately, the receiving slots 86, knife receiving slot 96 and/or tabs 78 may be omitted, and the wedge assemblies 72 and/or knife 90 are connected to the block 84 in a different way, such as by molding. Alternately, the wedge assemblies 72, knife 90 and block 84 may be fabricated as an integral unit. The block 84 may be generally shaped as a rectangular solid. Alternately, the block 84 may be shaped in any other suitable manner. A protrusion 98 may extend generally upward from the upper surface 88 of the block 84, at a location at or near the proximal end of the block 84. Alternately, the protrusion 98 may extend in a different direction and/or may extend from a different location on the block 84. The protrusion 98 may be generally shaped as a rectangular solid, but may be shaped in any other suitable manner. Alternately, the block 84 may be omitted, and the wedge assembly 72 and knife 90 may be controlled and/or manipulated in any other suitable manner.

At least part of the block 84 may be positioned in a space such as the recess 120 (FIG. 17A) defined within the end effector 4 and/or the shaft 6, and the block 84 may be longitudinally slidable along that space in order to control the motion of the wedge assemblies 72 and the knife 90. Alternately, the block 84 may be positioned differently relative to the end effector 4 and/or the shaft 6. Optionally, one or more sliders 100 may extend downward from the lower surface 102 of the block 84 to engage a corresponding feature or features in the end effector 4 and/or shaft 6 in order to facilitate sliding of the block 84. Alternately, the sliders 100 may be omitted. Referring also to FIG. 16, a rod 104 may be connected to the protrusion 98 in any suitable manner. As one example, the rod 104 may be molded into the protrusion 98. The distal end of the rod 104 may be connected to the protrusion 98, and the rod 104 may extend through the shaft 6 such that the proximal end of the rod 104 extends into the handle 8. The rod 104 may be generally rigid, and may extend generally longitudinally into the shaft 6 and/or through the shaft 6 to the handle 8. Alternately, the rod 104 may be flexible and/or threaded, and the rod 104 may engage corresponding threads provided in the protrusion 98 or other part of the block 84. In this way, rotation of the rod 104 causes the block 84 to advance or retract longitudinally.

Referring also to FIG. 15, the knife 90 may include a body 106 extending in the distal direction from the hook 92. Like the arm 76 of a wedge assembly 72, the body 106 of the knife 90 may be laterally thin, and longer than it is wide or high. Alternately, the body 106, and/or at least one arm 76, may be shaped differently. A blade 108 may be located at the distal end of the body 106. Advantageously, the knife 90 may be fabricated as a single, integral structure. However, the knife 90 may be assembled from a separate hook 92, body 106 and/or blade 108. The blade 108 may be configured in any suitable manner for cutting tissue. As one example, the blade 108 includes a cutting edge 110 along its upper edge, where that cutting edge 110 may be angled upward. moving proximally along the blade 108. Alternately, the cutting edge 110 may be oriented differently, or positioned differently on the blade 108. Referring also to FIG. 11, the knife 90 is movable along at least part of the space between the inner walls 68 of the housing 60. Part of each feeder belt 16 is positioned in each receiving space 70, laterally outward from the inner walls 68 of the housing 60. Thus, the knife 90 is movable longitudinally between two feeder belts 16.

Optionally, the blade 108 and/or cutting edge 110 of the knife 90 may be heated in order to cauterize tissue. Optionally, an electric current may be passed through the blade 108 of the knife 90 such that the blade 108 electrically cauterizes tissue. The blade 108 may be unipolar, or may be one pole of a bipolar system. Optionally, the knife 90 may be omitted, and in its place a wire may be used. The wire may be threaded distally into the staple holder 30, upward from the staple holder 30 into the anvil 32, then proximally out of the anvil 32. Proximal motion of the wire causes the wire to move through tissue, cutting it. The wire may be an electrode, such that electricity may be applied to it to facilitate both cutting and electrocauterization of tissue. The wire may be removed after each use and a new wire advanced, in order for the end effector 4 to be able to clamp another tissue structure, and to allow the wire to be replaced each time to maximize its cutting and/or cauterizing ability.

Referring also to FIG. 16, a cross-sectional view of the end effector 4 in an initial configuration is shown. The blade 108 of the knife 90 may be positioned entirely within the staple holder 30 in the initial configuration, to ensure that the cutting edge 110 does not incise tissue as the end effector 4 is moved to the surgical site. Further, the blade 108 may be positioned within the distal end 42 of the feeder belt guide 40 in the initial configuration. Alternately, the blade 108 may be positioned differently. In the initial configuration, the staples 18 may be positioned within the staple holder 30 in position for deployment, each located under a corresponding aperture 67 in the top plate 66. The block 84 is located in an initial position corresponding to the initial position of the blade 108 and the wedge assemblies 72. Advantageously, in the initial configuration, the wedge assemblies 72 and the knife 90 are each in their most-distal position. However, at least one wedge assembly 72 and/or the knife 90 may be positioned differently in the initial position.

Figure 17:
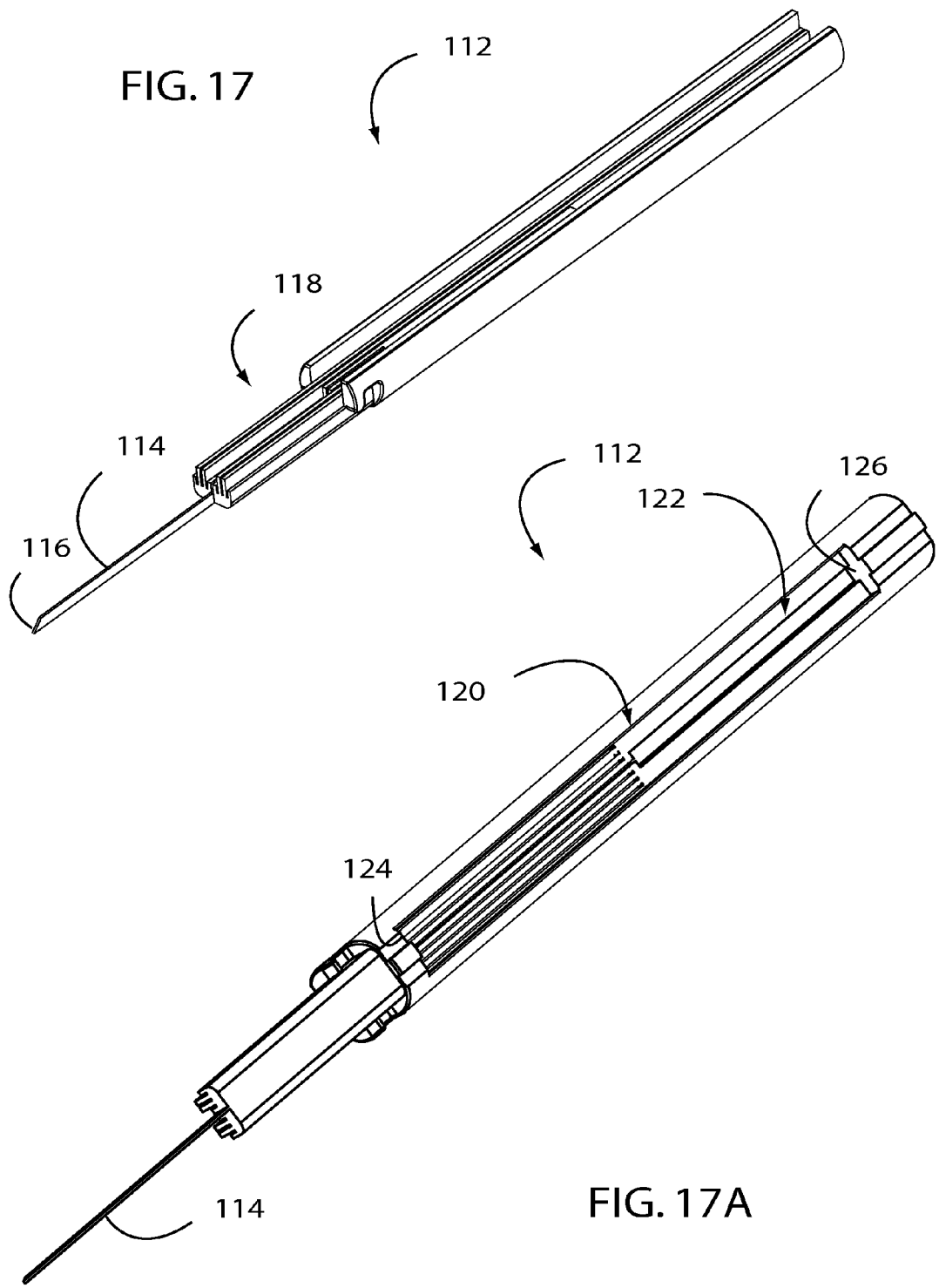
FIG. 17 is a perspective view of a retainer of the exemplary end effector of FIG. 7.

Referring also to FIG. 17, a retainer 112 may be positioned between the end effector 4 to the shaft 6. Optionally, the retainer 112 may provide a connection between the end effector 4 and the shaft 6, such as by friction or interference fitting with both the end effector 4 and the shaft 6, or by otherwise connecting both the end effector 4 and the shaft 6 to the retainer 112. Alternately, the retainer 112 may be positioned entirely within the end effector 4. The retainer 112 may be shaped in any suitable manner. The retainer 112 may include an extension 114 protruding distally from a first body segment 118, where the extension 114 includes a ramp 116 at the distal end thereof. The ramp 116 may be angled upward in the proximal direction. The ramp 116 may be generally linear. Alternately, the ramp 116 may be oriented differently, and may be curved or otherwise shaped. The first body segment 118 may be shaped and sized to be received in the proximal end of the housing 60, and at least part of the first body segment 118 may extend into the proximal end of at least one receiving space 70 of the housing 60. The first body segment 118 may be fixed to the housing 60, such as by pressure or interference fitting, by adhesive, by welding, or by any other suitable mechanism or method. Alternately, the first body segment 118 is not fixed to the housing 60. Alternately, the retainer 112 is not fixed or connected to the housing 60. Alternately, the retainer 112 may be omitted. Optionally, at least part of the feeder belt guide 40 may be connected to the retainer 112 as well. As one example, the insert 43 of the feeder belt guide 40 may extend completely through a receiving space 70 in the housing 60 and into contact with the retainer 112. If so, the feeder belt guide 40 may be connected to the retainer 112 in any suitable manner.

Referring also to FIG. 17A, the underside of the retainer 112 may include a recess 120 defined therein. The recess 120 may be shaped and sized to allow the block 84 to slide therein. The recess 120 may include a slot 122 defined therethrough, where the slot 122 may receive the protrusion 98 and allow the protrusion 98 to slide therein. The recess 120 and/or slot 122 may guide the motion of the block 84 longitudinally and restrict motion of the block 84 proximal or distal to certain locations, and may also or instead restrict lateral motion of the block 84. For example, the recess 120 may include a distal wall 124 that contacts the distal end of the block 84 when the block 84 has advanced distally as far as desired, and a proximal wall 126 that contacts the proximal end of the block 84 when the block 84 has retracted proximally as far as desired. Alternately, the recess 120 may be defined in a different part of the retainer 112, or may be omitted.

Figure 30:
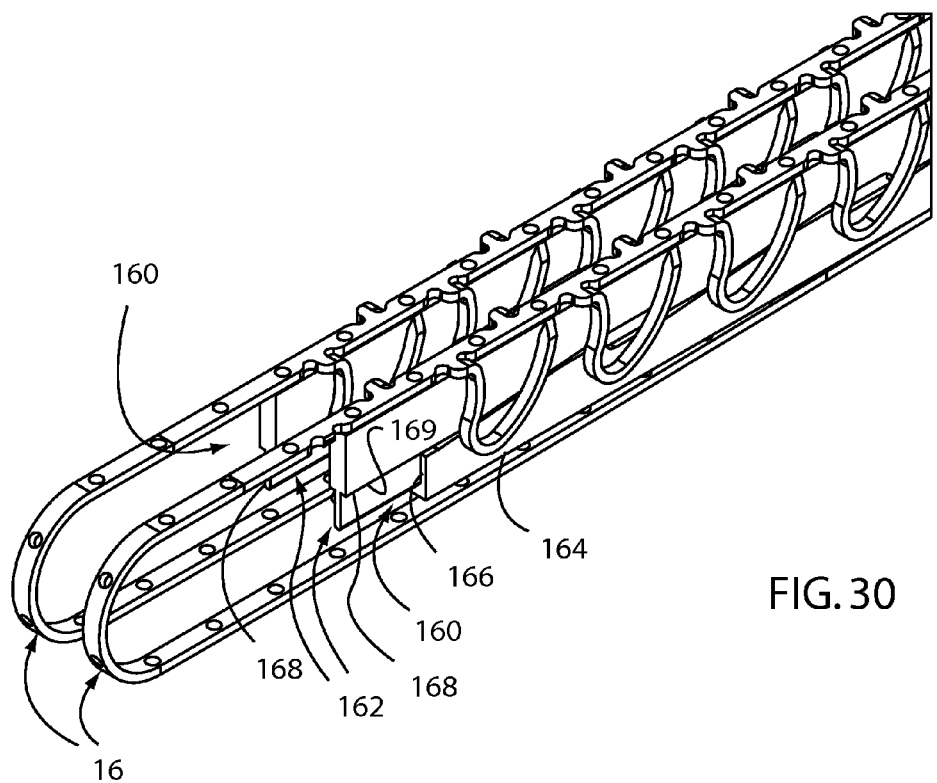
FIG. 30 is a perspective view of sliding clamps, each in a first position relative to a corresponding feeder belt.

Referring to FIG. 30, optionally sliding clamps 160 may be provided, where each set of sliding clamps 160 may be associated with a corresponding feeder belt 16. Each set of sliding clamps 160 may include an upper clamp 162 and a lower clamp 164, where at least one of the clamps 162, 164 is slidable relative to the other. The lower clamp 164 may have a slot 166 defined generally longitudinally therein and oriented generally upward. The upper clamp 162 may have a tongue 168 oriented generally downward, where the tongue 168 is sized and configured to be received in the slot 166 in the lower clamp 164. The tongue 168 may be narrower than the remainder of the upper clamp 162, or may be sized in any other suitable manner. The wider area of the upper clamp 162 from which the tongue 168 extends forms a ledge 169 at its lower surface. The upper surface of the upper clamp 162 may be substantially as wide as the feeder belt 16.

Figure 31:
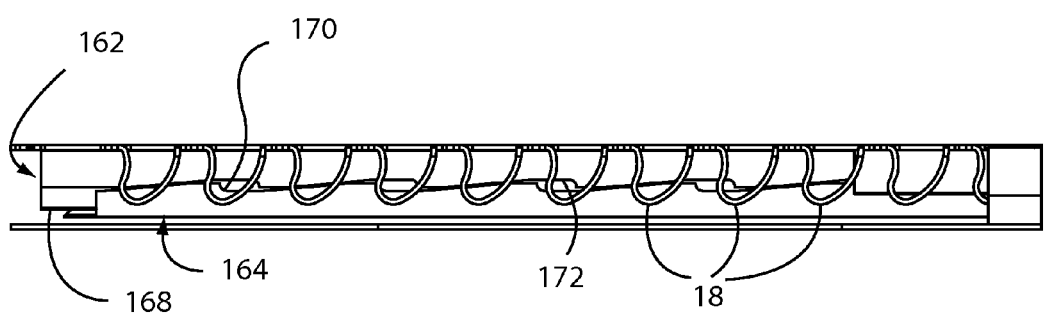
FIG. 31 is a side view of the sliding clamps of FIG. 30, each in a first position relative to a corresponding feeder belt.
Figure 32:
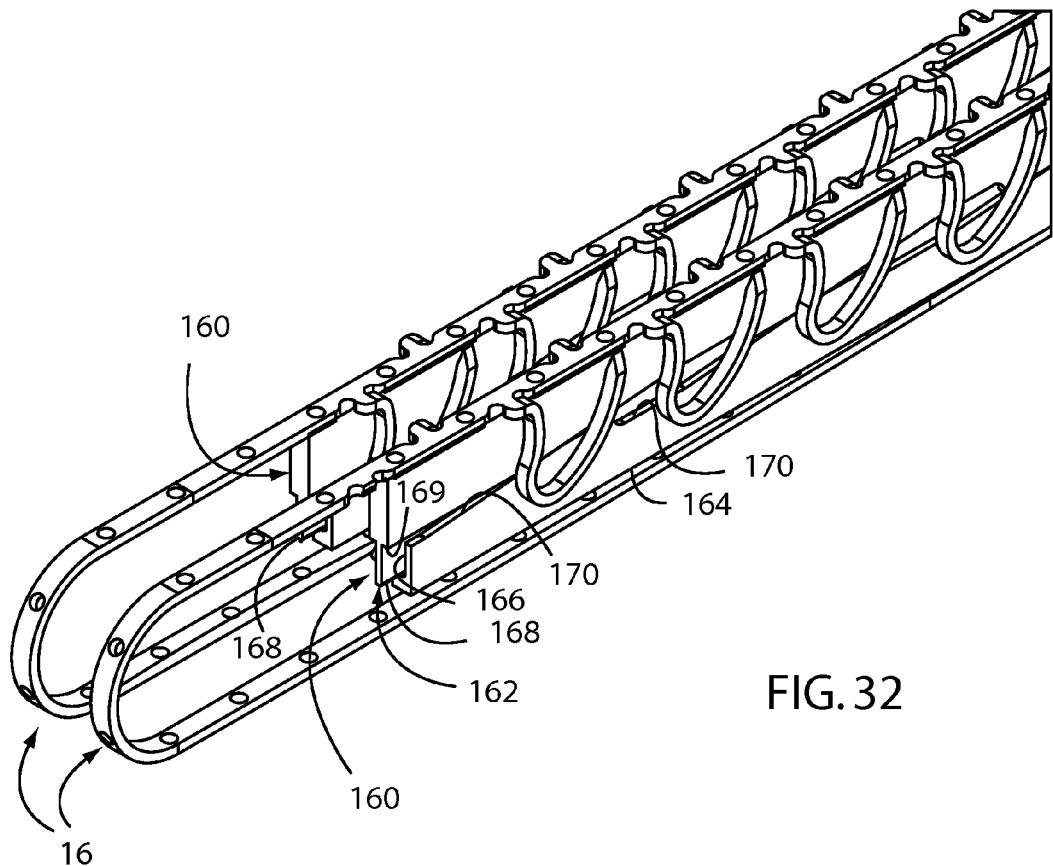
FIG. 32 is a perspective view of the sliding clamps of FIG. 30, each in a second, clamping position relative to a corresponding feeder belt.
Figure 33:
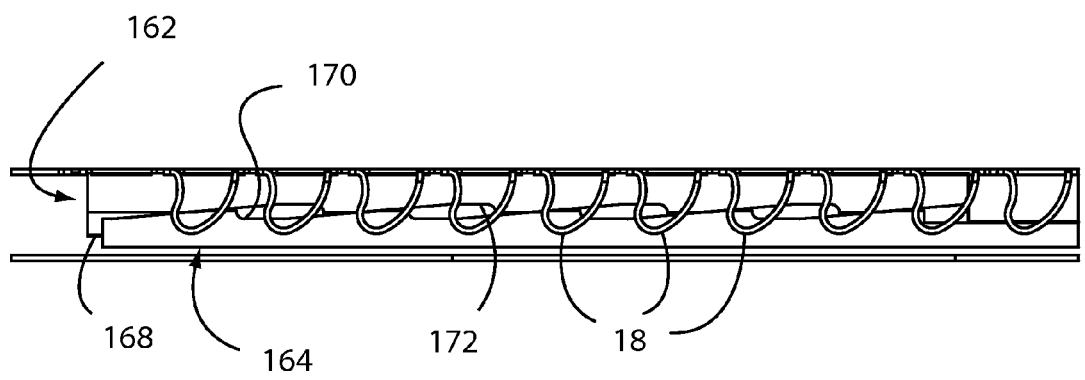
FIG. 33 is a side view of the sliding clamps of FIG. 30, each in a second, clamping position relative to a corresponding feeder belt.

Referring also to FIG. 31, initially the distal end of the upper clamp 162 may extend further in the distal direction than the distal end of the lower clamp 164. Alternately, the distal end of the lower clamp 164 initially may extend further in the distal direction than the distal end of the upper clamp 162. Alternately, initially the distal ends of each clamp 162, 164 may extend substantially the same distance in the distal direction. The upper surface of the lower clamp 164 may have a cam surface 170 defined thereon. Similarly, the ledge 169 of the upper clamp 162 may be shaped to define a cam surface 172 thereon. The two cam surfaces 170, 172 engage one another such that, in the initial position of the two clamps 162, 164, the height of the upper clamp 162 is lower than the height of the upper portion of the corresponding feeder belt 16; as a result, the feeder belt 16 can be advanced without being restrained by the upper clamp 162. Referring also to FIGS. 32-33, the cam surfaces 170, 172 are shaped such that, as the upper clamp 162 is retracted proximally and/or the lower clamp 164 is advanced distally, the upper clamp 162 is pushed upward into contact with the feeder belt 16. Such contact provides additional support for the feeder belt 16 during deployment of the staples 18.

Endocutter—Two Staple Rows

Figure 18:
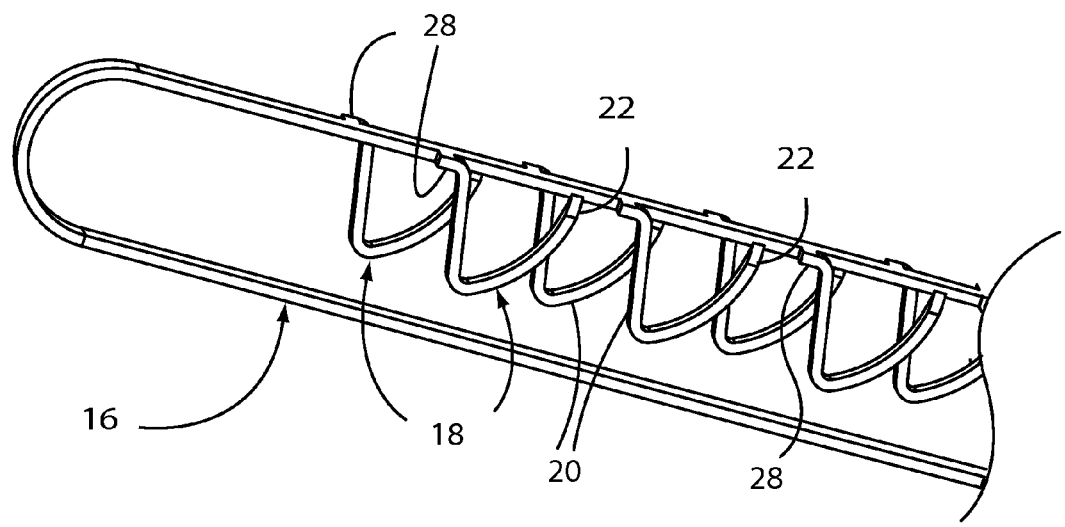
FIG. 18 is a perspective view of an exemplary feeder belt with two rows of staples frangibly connected thereto.
Figure 19:
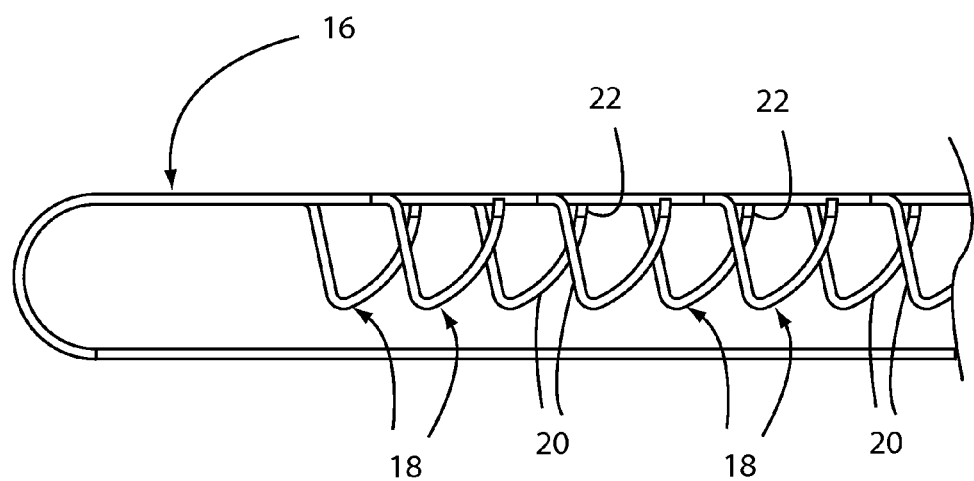
FIG. 19 is a side view of the feeder belt of FIG. 18.
Figure 20:
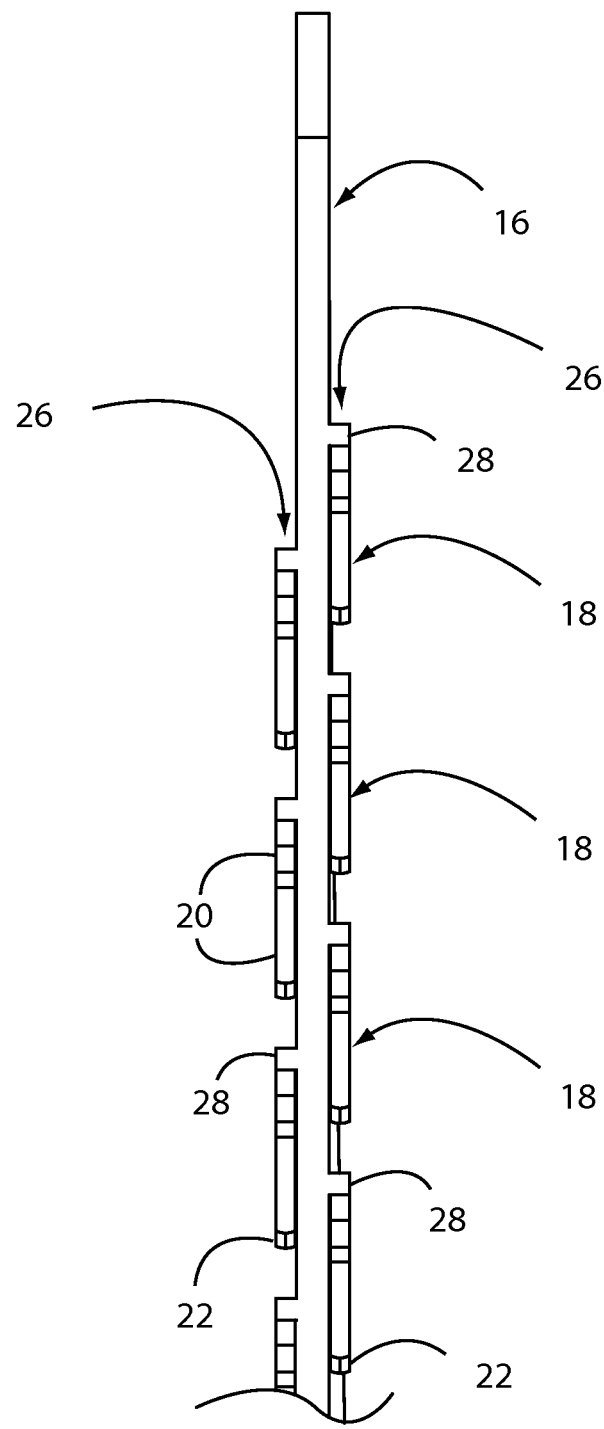
FIG. 20 is a top view of the feeder belt of FIG. 18.

Referring also to FIG. 6, the endocutter 2 described above includes an end effector 4 configured to place two or more sets of three rows 26 of staples 18. However, the end effector 4 may be configured to place two or more sets of different numbers of rows 26 of staples 18, such as by changing the number of rows 26 of staples 18 on the one or more feeder belts 16. Such an end effector 4 may be configured generally as described above. As one example, referring to FIGS. 18-20, a feeder belt 16 may include two rows 26 of staples 18. With such a feeder belt 16, one row 26 of staples 18 may be located along each side of the feeder belt 16. As a result, the feeder belt 16 may be narrower than a feeder belt 16 in which a third row 26 of staples 18 extends along the center portion of the feeder belt 16. Thus, by reducing the number of rows 26 of staples 18, the end effector 4 may be reduced in size. For example, the end effector 4 described above as having three rows 26 of staples 18 may be sized to fit through a trocar port 10 having a 10 mm diameter passage therethrough, and an end effector 4 having two rows 26 of staples 18 may be sized to fit through a trocar port 10 having a 5 mm diameter passage therethrough. Referring to FIGS. 18-20, the staples 18 may be shaped, and positioned relative to the feeder belt 16, substantially as described above with regard to the feeder belt 16 having three rows 26 of staples 18. Alternately, the staples 18 may be shaped differently and/or positioned in any other suitable manner relative to the feeder belt 16. The staples 18 may be frangibly connected to the feeder belt 16 substantially as described above. Alternately, the staples 18 may be connected to the feeder belt 16 in any other suitable manner.

At least two staples 18 in different rows 26 may be staggered relative to one another. That is, at a given longitudinal position along the feeder belt 16 at which a staple 18 in one row 26 is attached to the feeder belt 16, the other row 26 does not have a staple 18 attached to the feeder belt 16. This staggering of the staples 18 promotes hemostasis in tissue treated with the end effector 4. Alternately, staples 18 in each row 26 may be aligned with one another, such that at a given longitudinal position along the feeder belt 16 at which a staple 18 in one row 26 is connected to the feeder belt 16, each other row 26 has a staple 18 connected to the feeder belt 16 as well.

The staples 18 in each row 26 may be substantially evenly spaced apart from one another. That is, the distance between any two longitudinally-adjacent staples 18 in a row is substantially the same. Alternately, at least two longitudinally-adjacent staples 18 in each row 26 may be spaced apart a distance different from the distance between two other longitudinally-adjacent staples 18. Such a configuration may be useful where the length of the staple line is not adjustable. The staple line to be created with the end effector 4 may be fixed at a particular number of staples 18, and the staples 18 in each row may be grouped together in groups each having a length substantially the same as that fixed staple line. Each group of staples 18 in a row 26 may thus be separated from the adjacent group of staples 18 by a blank space on the feeder belt 16, where that blank space may have any suitable length.

Figure 21:
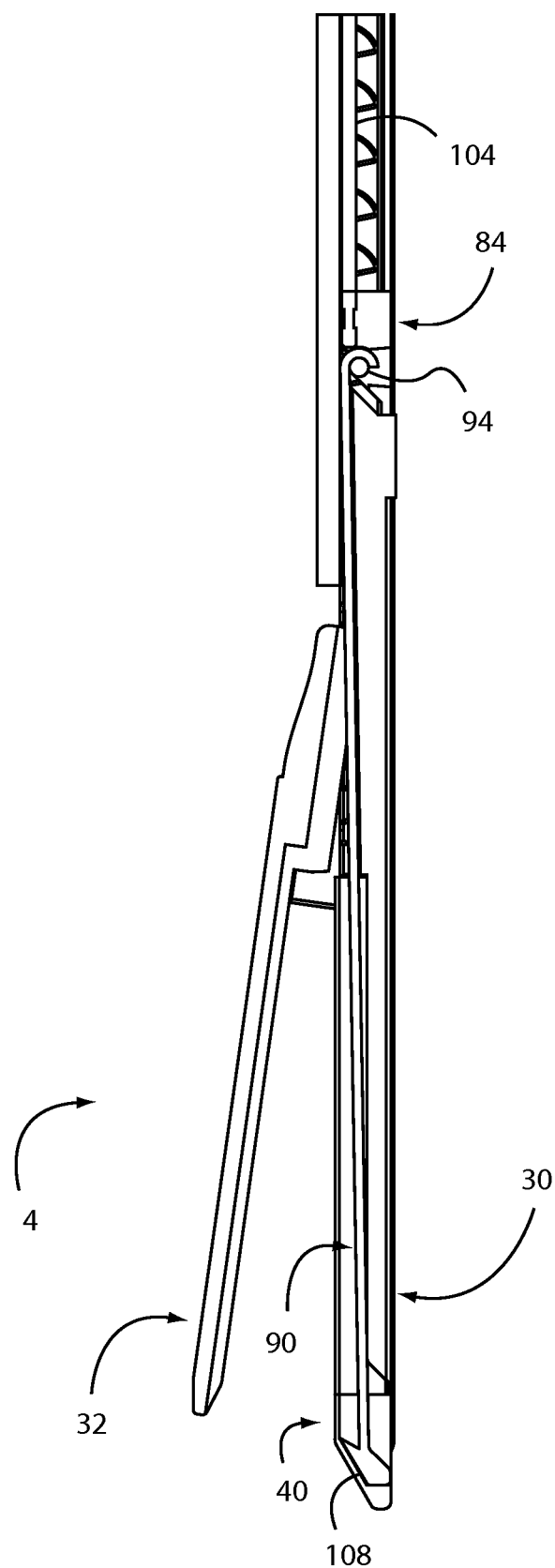
FIG. 21 is a side cross-section view of an exemplary end effector of an endocutter that utilizes the feeder belt of FIGS. 18-20.
Figure 22:
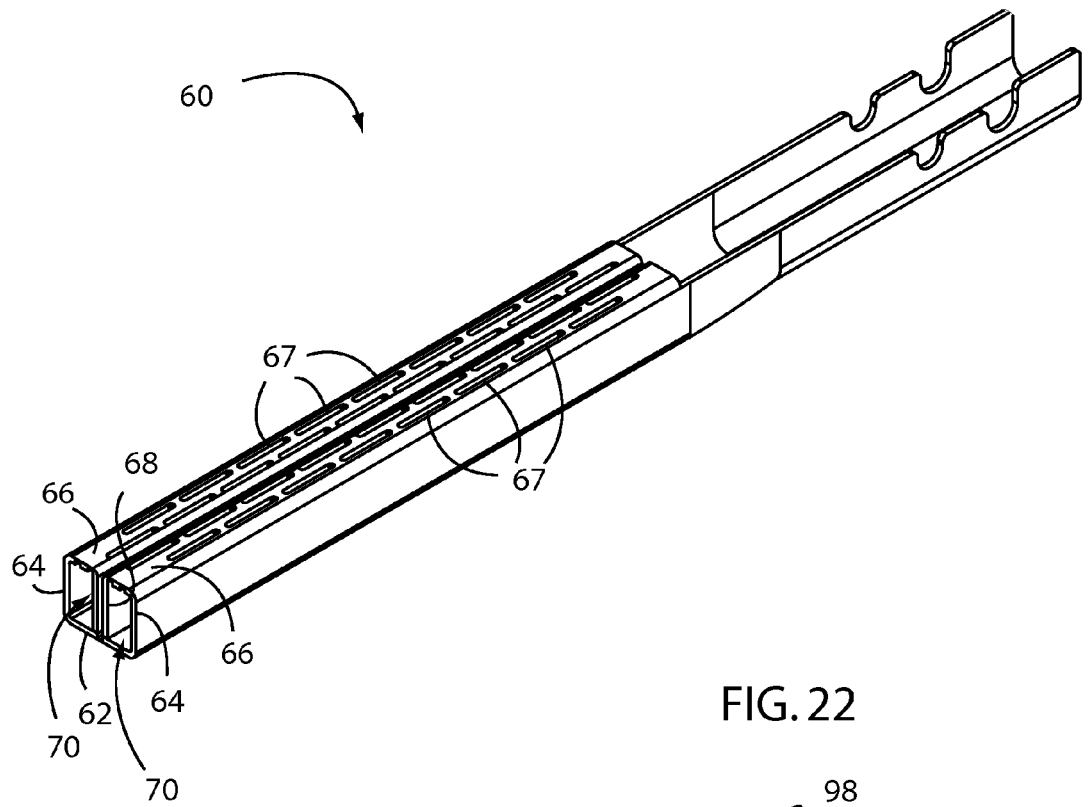
FIG. 22 is a perspective view of an exemplary housing of a staple holder of the exemplary end effector of FIG. 21.
Figure 23:
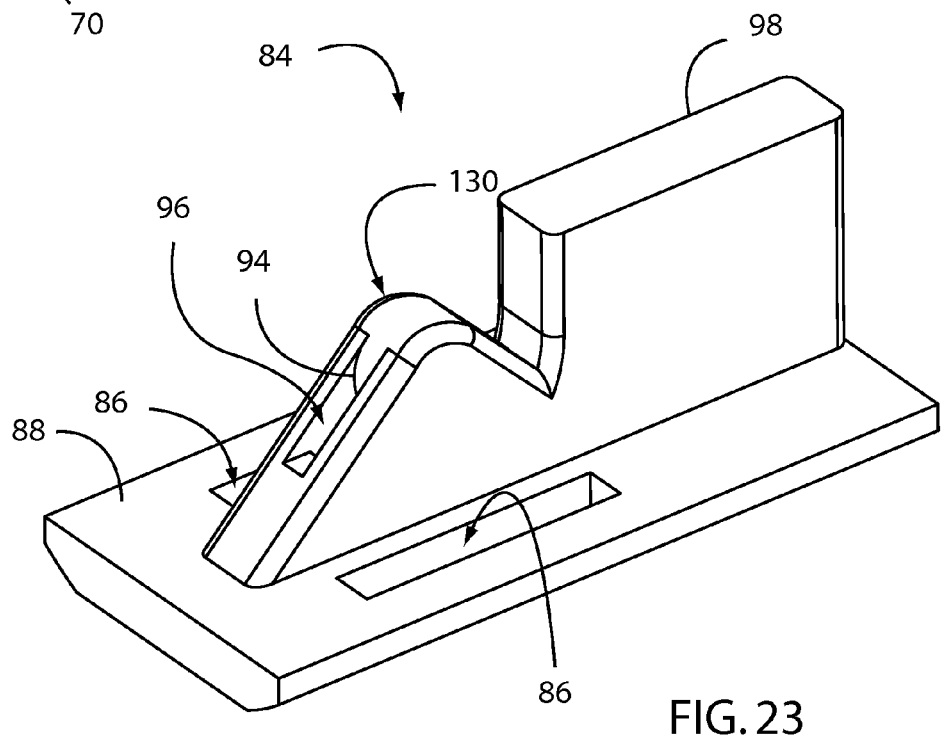
FIG. 23 is a perspective view of a block of the exemplary end effector of FIG. 21.
Figure 24:
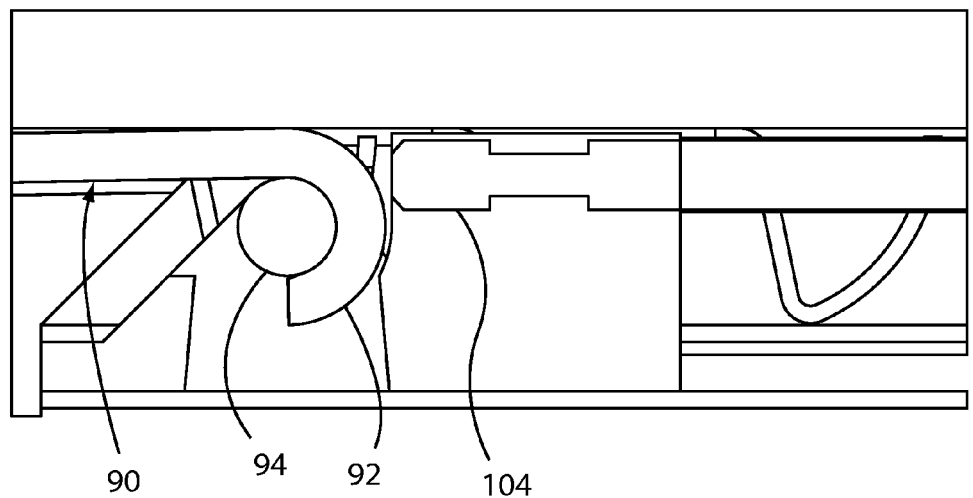
FIG. 24 is a detail cross-section view of the exemplary end effector of FIG. 21 in the vicinity of the block.

Referring to FIG. 21, the configuration of the end effector 4 utilizing feeder belts 16 each having two rows 26 of staples 18 is similar to the configuration of the end effector 4 utilizing feeder belts 16 each having three rows 26 of staples 18, as shown in FIG. 16. Referring to FIG. 22, the housing 60 may be configured similarly to the housing of FIG. 11. The housing 60 includes two rows of apertures 67 in each top plate 66, corresponding to the two rows 26 of staples 18 of each feeder belt 16. Due to the presence of two, rather than three, rows of apertures 67 in each top plate 66, the top plates 66 and thus the housing 60 overall may be narrower than the housing of FIG. 16. Optionally, at least part of the housing 60 may omit the top plates 66 and/or inner walls 68. Referring to FIGS. 23 and 24, the block 84 optionally may be configured differently than the block 84 of FIG. 14, in order to fit within a narrower end effector 4. The projection 98 may be longer in the longitudinal direction than the projection 98 of the block 84 of FIG. 14. The distal end or other portion of the rod 104 may be attached to the protrusion 98 in any suitable manner. As one example, the rod 104 may be molded into the protrusion 98. A riser 130 may extend upward from the upper surface 88 of the block 84, where a knife receiving slot 96 may be defined generally longitudinally in the riser 130. The riser 130 may be generally triangular, or may be any other suitable shape. Optionally, the riser 130 may be connected to or part of the protrusion 98 that engages the rod 104. A pin 94 may extend laterally across the knife receiving slot 96 of the riser 130, and engages the hook 92 at the proximal end of the knife 90. Alternately, the block 84 may be omitted.

Figure 23A:
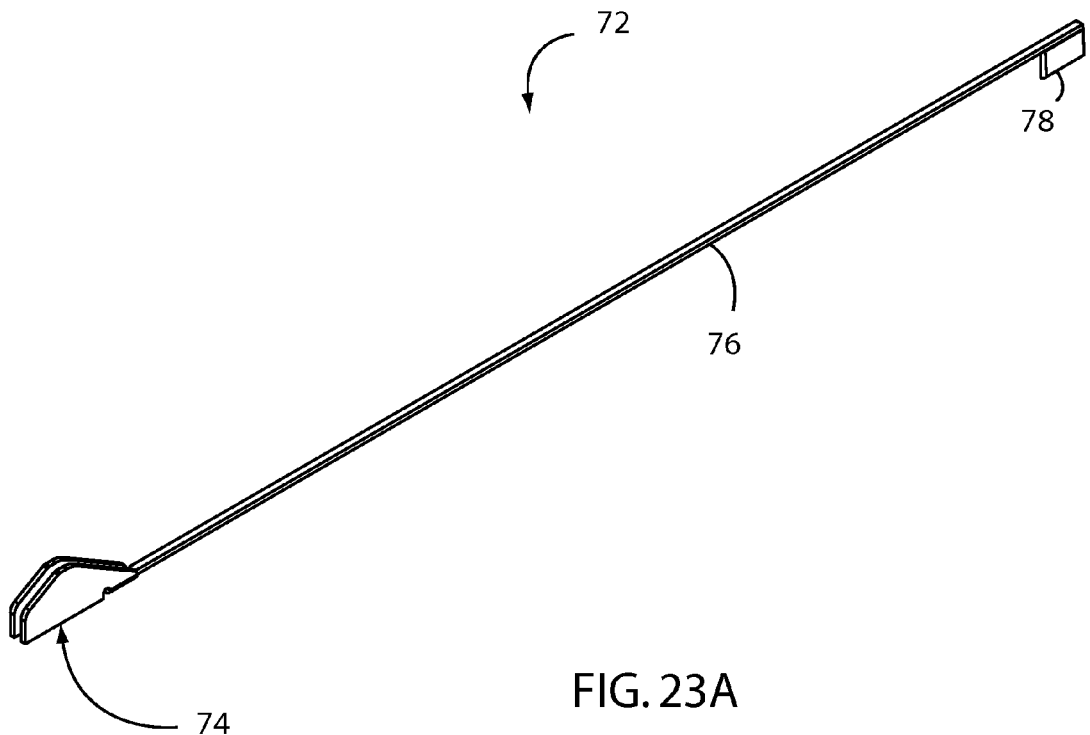
FIG. 23A is a perspective view of a wedge assembly.

Two receiving slots 86 may be defined partially into, or completely through, the block 84, generally as described with regard to FIG. 14 above. Referring also to FIG. 23A, another example of a wedge assembly 72 is shown. The wedge assembly 72 includes a tab 78 and an arm 76, as with the wedge assembly 72 of FIG. 14. However, the wedge assembly 72 of FIG. 23A includes two or more wedges 74 at its distal end, where the wedges 74 may be spaced apart laterally from one another and may be generally parallel to one another. In this way, multiple wedges 74 can be controller by a single arm 76, reducing the number of parts needed in the end effector 4 and allowing the end effector 4 to be made narrower. The wedges 74 may be shaped as set forth with regard to FIG. 14, or may be shaped in any other suitable manner. The tab 78 of each wedge assembly 72 of FIG. 23A may be inserted into a corresponding receiving slot 86 in the block 84 of FIG. 23. Alternately, four receiving slots 86 may be provided in the block 84 of FIG. 23, and the wedge assemblies 72 of FIG. 14 may be used. Alternately, the block 84 may be configured generally as described above and shown in FIG. 14.

Two exemplary embodiments of the end effector 4 have been described above, and in each one the end effector 4 places two sets of rows 26 of staples 18. However, the end effector 4 may be configured to place one set, or three or more sets, of rows 26 of staples 18. Further, the feeder belt 16 may be configured to place any desired number of rows 26 of staples 18 within a given set of rows 26. Further, any number of feeder belts 16 may be placed on either side of the knife 90. The number of feeder belts 16 on one side of the knife 90 may be the same as, or different from, the number of feeder belts 16 on the other side of the knife 90. The number of feeder belts 16 utilized may be related to the type of tissue that is treated by the end effector 4. The number of rows 26 of staples 18 may be different on each feeder belt 16, or may be the same on each feeder belt 16. The number of rows 26 of staples 18 on an individual feeder belt 16 may vary along the length of that feeder belt 16, or may be constant. As another example of an end effector 4, the knife 90 may be omitted, such that the end effector 4 is simply a stapler that does not cut tissue. If so, any suitable number of feeder belts 16 may be utilized.

Figure 25:
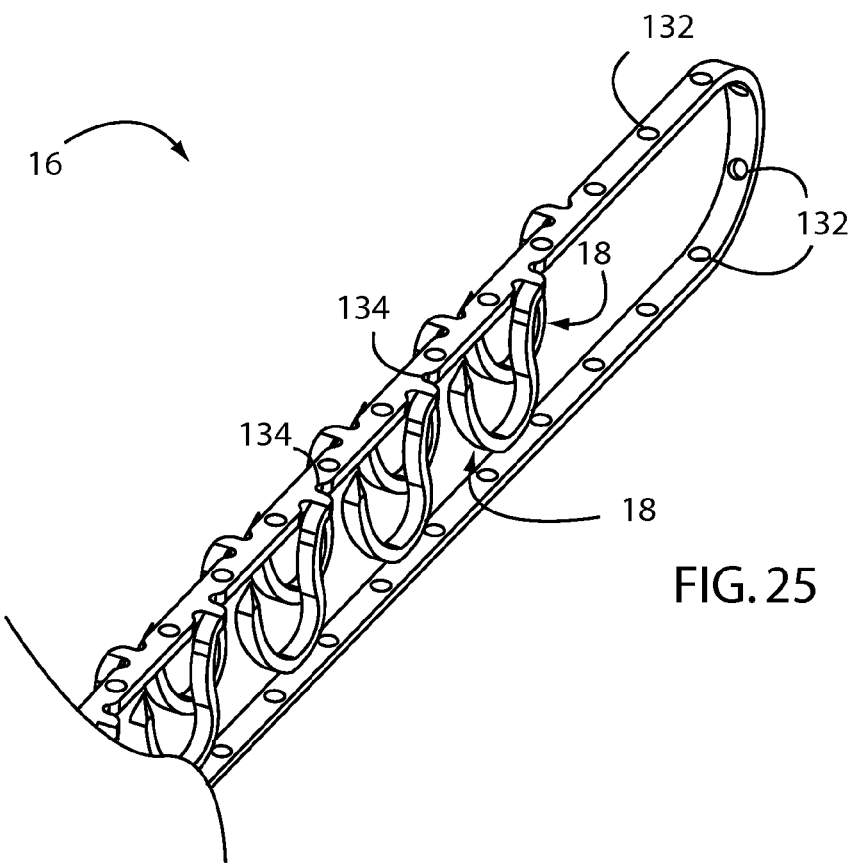
FIG. 25 is a perspective view of another exemplary feeder belt with two rows of staples frangibly connected thereto.
Figure 26:
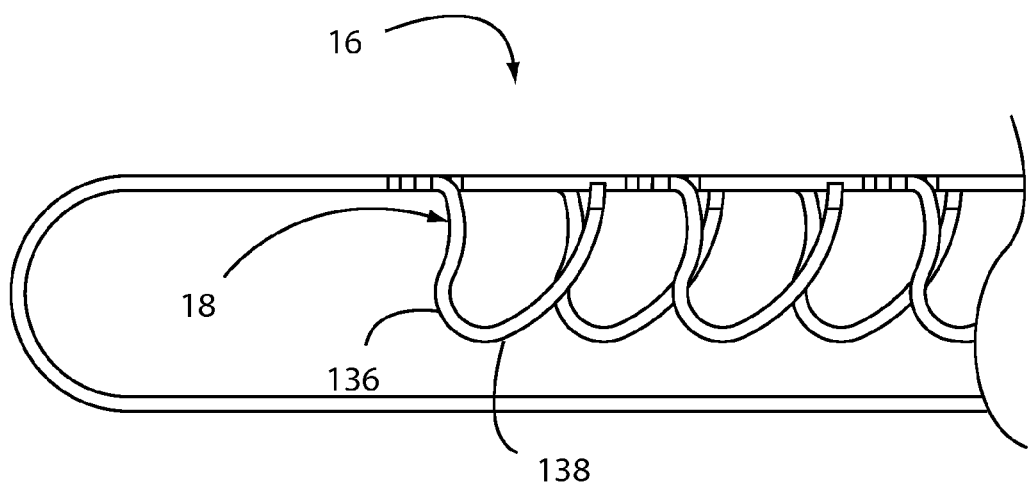
FIG. 26 is a side view of the feeder belt of FIG. 25.
Figure 27:
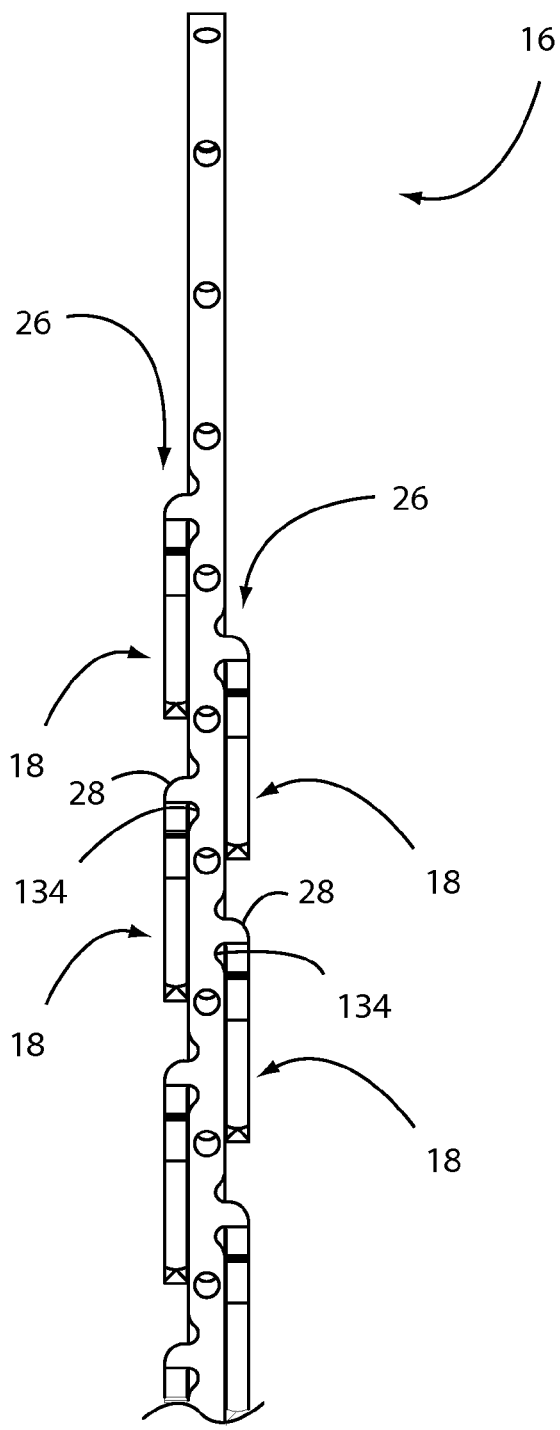
FIG. 27 is a top view of the feeder belt of FIG. 25.

Referring to FIGS. 25-27, another exemplary feeder belt 16 having two rows 26 of staples 18 is shown. This feeder belt 16 may include a plurality of openings 132 defined therein or therethrough. The openings 132 may be round, or any other suitable shape. The openings may all be of substantially the same size and/or shape, and/or may be of different sizes and/or shapes. The openings 132 may be useful in reducing the moment of inertia of the feeder belt 16 such that the feeder belt 16 is more flexible and more easily slides along the nose 50 of the staple holder 30. Instead, or in addition, one or more of the openings 132 may be engaged by pins or gears (not shown) in the handle 8 of the endocutter 2 in order to cause the feeder belt 16 to move. In addition to, or instead of, the openings 132, the feeder belt 16 may have one or more notches 134 defined in one or more lateral edges thereof Each notch 134 may be located adjacent to a tab 28, or one or more notches 134 may be located differently. The notches 134 also may act to increase the flexibility of the feeder belt 16, and/or to promote engagement between a mechanism in the handle 8 and the feeder belt 16.

At least one staple 18 may be shaped as a continuous curve, as may be most clearly seen in FIG. 26. A distal end of the staple 18 may be connected to the feeder belt 16, such as via a tab 28 protruding laterally from the feeder belt 16, such as described above. The staple 18 may extend proximally and downward from the tab 28. Then, the staple 18 may continue to curve downward, but also curve distally to form a bump 136. This bump 136 may extend to the longitudinal position of the tab 28, further distally than the longitudinal position of the tab 28, or not as far longitudinally as the tab 28. Then, the staple 18 may continue to curve downward, but also curve proximally. The staple 18 continues to curve proximally, then begins to curve upward at an inflection point 138. The staple 18 then continues to curve upward and proximally until terminating at a free end 22 at its proximal end.

Figure 28:
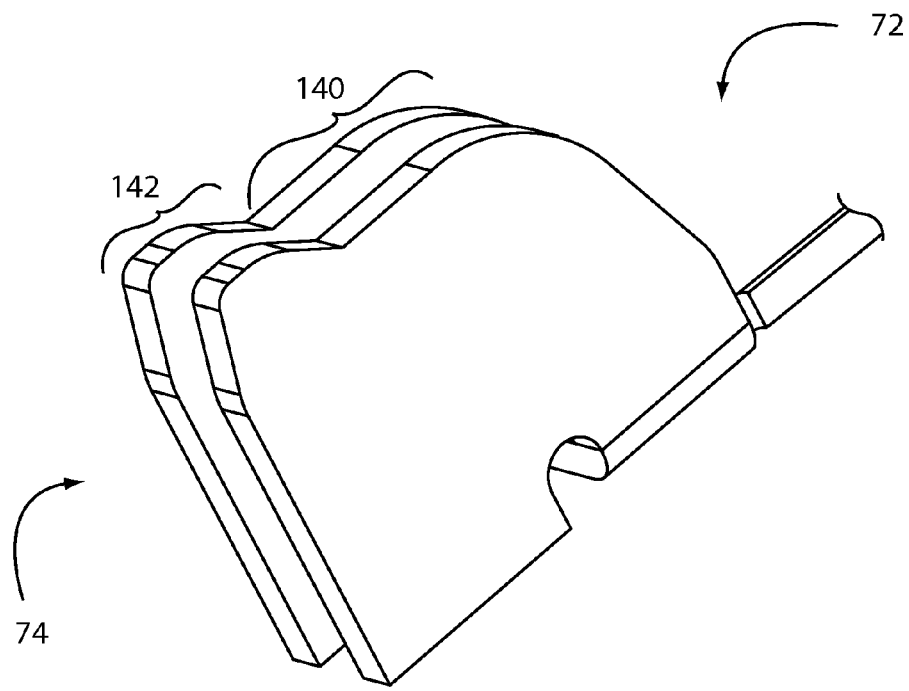
FIG. 28 is a perspective view of the distal end of another exemplary wedge assembly.

Referring also to FIG. 28, the wedge 74 of a wedge assembly 72 may have a shape that facilitates deployment of the staples of FIGS. 25-27. The wedge 74 may have a first segment 140 shaped to facilitate deployment of the staple 18, and a second segment 142 shaped to facilitate shearing or otherwise separating the staple 18 from the feeder belt 16. The first segment 140 is curved upward and distally; the curve may have any shape that facilitates formation of a staple 18. By providing two distinct segments 140, 142 on the wedge 74, formation and separation of the staple 18 can be separately controlled.

Operation

Referring to FIGS. 2-3, at least one trocar port 10 is inserted into an opening in tissue 12 of a patient 14. Where a trocar port 10 includes a cutting tool (not shown) such as a spike, that cutting tool makes an opening in tissue 12, after which the trocar port 12 is placed in tissue. The cutting tool may be removed from the trocar port 10 after the trocar port 10 is in position in tissue 12. Alternately, an opening in tissue 12 may be made first with a separate tool, and the trocar port 10 is then placed in that opening. Multiple trocar ports 10, having the same or different cross-sectional shapes and/or areas, may be placed in the patient 14. The tissue 12 may be the chest wall of the patient 14, thereby providing access to the thoracic cavity. However, the tissue 12 may be the abdominal wall or any other suitable tissue in the patient 14. Alternately, the trocar port or ports 10 are not used, and access to the surgical site is gained in another manner, such as described above.

Referring also to FIGS. 1, 16 and 21, the end effector 4 of the endocutter 2 is introduced into the patient 14 through one of the trocar ports 10. At least part of the shaft 6 of the endocutter 2 may follow the end effector 4 into the patient 14. Alternately, the trocar port or ports 10 are not used, and the endocutter 2 is used during a conventional open surgical procedure or is introduced into the patient 14 directly through an incision in tissue 12. The end effector 4 is positioned by the user at a surgical site. As one example, referring also to FIG. 29, a surgical site is located on a blood vessel 148 which is to be transected. For clarity, this document describes the operation of the endocutter 2 for transection of a blood vessel 148. However, the use of the endocutter 2 is not limited to blood vessel transection; the endocutter 2 may be used to perform any other suitable procedure at any other surgical site in the body. For example, the endocutter 2 may be used to transect a bile duct, to remove a diseased appendix, to transect gastrointestinal tissue, and/or to transect soft tissue or organs.

Referring to FIGS. 16 and 21, at least the distal end of the anvil 32 is initially spaced apart from the staple holder 30, such that the end effector 4 is open. The end effector 4 is advanced over the blood vessel 148 to be transected, until the entire diameter of the blood vessel 148 is located between the anvil 32 and the staple holder 30. Advantageously, the blood vessel 148 is substantially at a right angle to the anvil 32 and the staple holder 30. However, the blood vessel 148 may be oriented at any other suitable angle relative to the anvil 32 and the staple holder 30. The end effector 4 is then closed, by moving the anvil 32 closer to the staple holder 30, such that the blood vessel 148 is compressed between the anvil 32 and the staple holder 30. Such closure of the end effector 4 may be accomplished in any standard manner or any other suitable manner. As one example, a tube may be advanced distally over the outer surface of both the anvil 32 and the staple holder 30, compressing the anvil 32 and the staple holder 30 together. Alternately, the anvil 32 may be substantially fixed relative to a remainder of the end effector 4 and/or the shaft 6, and the staple holder 30 may be moved closer to the anvil 32 in order to close the end effector 4. Alternately, both the anvil 32 and the staple holder 30 are movable toward one another in order to close the end effector 4. Closure of the end effector 4 may be performed by actuating one or more controls on the handle 8 of the endocutter 2, and/or by releasing energy stored in the handle 8. After the end effector 4 has been closed, the tissue to be treated is held securely by, and affirmatively controlled by, the end effector 4.

Referring also to FIGS. 6 and 12, the wedges 74 are in an initial position, in which each wedge 74 may be distal to the staples 18 in the corresponding row 26. Further, referring also to FIG. 11, at least one staple 18 in each row 26 initially is positioned under a corresponding aperture 67 in the top plate 66 of the housing 60. Advantageously, a staple 18 initially is positioned under each aperture 67 in the top plate 66 of the housing 60. Referring to FIGS. 14 and 17A, the block 84 is located at or in proximity to the distal wall 124 of the recess 120, which is the initial position of the block 84. Alternately, in its initial position the block 84 may be located at or in proximity to a proximal end of the recess 120, or may be located differently relative to the recess 120. In a staple holder 30 utilizing the block 84 of FIG. 23, the block 84 may be in an initial position in the staple holder 30 and/or shaft 6 of the endocutter 2, where the block 84 is at or in proximity to a distal end of a recess or space in the staple holder 30 and/or shaft 6. Alternately, the block 84 may be positioned at or in proximity to a proximal end of a recess or space in the staple holder 30 and/or shaft 6, or may be positioned differently relative to the staple holder 30 and/or shaft 6. Referring to FIGS. 15, 16 and 21, the knife 90 is in an initial position relative to the staple holder 30, where the cutting edge 110 of the knife 90 may be held completely within the staple holder 30. At least part of the blade 108 may be held within the staple holder 30 as well. Referring also to FIG. 8, the blade 108 and cutting edge 110 of the knife 90 may be located within the distal end 42 of the feeder belt guide 40.

The user then actuates one or more controls on the handle 8 to actuate the end effector 4. As a result, the rod 104 is moved proximally by any suitable mechanism or method. As one example, the proximal end of the rod 104 extends into the handle 8, and a mechanism within the handle 8 moves the rod 104 proximally. The mechanism may be actuated by a release of energy stored within the handle 8. A mechanism for moving a rod 104 linearly is standard; any suitable mechanism or mechanisms may be utilized. Proximal motion of the rod 104 causes the block 84 to move proximally, as a result of the attachment between the rod 104 and the protrusion 98 from the block 84. The proximal motion of the block 84 in turn causes the wedge assemblies 72 and knife 90, which are attached to the block 84, to move proximally. Alternately, the rod 104 may be rotated instead of, or in addition to, being retracted proximally, where such rotation causes proximal motion of the block 84.

If the sliding clamps 160 are used, and they have not been moved to the second position, in which the upper clamp 162 contacts the feeder belt 16, the sliding clamps 160 are moved to the second position. Such motion may include sliding the upper clamp 162 proximally and/or sliding the lower clamp 164 distally. During the sliding motion, the tongue 168 of the upper clamp 162 slides along the slot 166 of the lower clamp 164. As the upper clamp 162 and/or lower clamp 164 slide, the cam surfaces 170, 172 engage one another to cause the upper surface of the upper clamp 162 to move upward into contact with the feeder belt 16. Such contact further stabilizes the feeder belt 16 during contact between the wedges 74 and the staples 18.

Proximal motion of the wedge assemblies 72 in turn causes proximal motion of each wedge 74, which in turn causes deployment of the staples 18. For clarity, motion of a single wedge 74 to deploy one or more staples 18 in a corresponding row 26 is described. The wedge 74 may be initially distal to the staples 18 in the corresponding generally-linear row 26, and the path of motion of the wedge 74 may be generally parallel to or collinear with the corresponding row 26. As the wedge 74 moves proximally, the first surface 79 of the wedge 74 contacts the distalmost staple 18 in the corresponding row. Referring also to FIG. 5, contact between the first surface 79 and the staple 18 results in the application of force to the staple 18. Because the first surface 79 is angled upward in the distal direction, that force applied to the staple 18 is exerted both proximally and upward. Further, the force applied to the staple 18 results in a moment about the tab 28 that connects the staple 18 to the feeder belt 16. The moment acts on the staple 18 to rotate the staple 18 about the tab 28, such that the free end 22 of the staple 18 moves upward, out of the corresponding aperture 67 in the top plate 66 of the housing 60 and into the blood vessel 148. Alternately, where the tab 28 is not used, the force applied to the staple 18 results in a moment about the location of the connection of the staple 18 to the feeder belt 16. During motion of the wedge 74, the feeder belt 16 may be held substantially in place, either passively such as by friction with the corresponding nose 50, or actively such as by a brake or clutch (not shown) in the handle 8, shaft 6 and/or end effector 4.

The wedge 74 continues to move proximally, continuing to exert a force on the staple 18 that causes a moment about the tab 28. As the free end 22 of the staple 18 rotates upward, it penetrates completely through the blood vessel 148 and then contacts the lower surface of the anvil 32. Optionally, a standard staple bending feature (not shown) may be defined in the anvil 32 at the location where the free end 22 of the staple 18 contacts the anvil 32. As the free end 22 of the staple 18 contacts the anvil 32, the rotation of the staple 18 about the tab 28 results in motion of the free end 2 both upward and distally. However, contact between the free end 22 of the staple 18 and the anvil 32 prevents further upward motion of the free end 22 of the staple 18. As a result, the free end 22 of the staple 18 moves distally along the lower surface of the anvil 32 and/or staple bending feature defined thereon. This motion may bend or deform the leg 20 of the staple 18 associated with the free end 22, closing the staple 18. The staple 18 may be fabricated from a plastically-deformable material such as stainless steel, such that deformation of the staple 18 may be plastic deformation. Alternately, at least part of at least one staple 18 may be elastically deformable or superelastically deformable.

As the wedge 74 continues to move proximally, the peak 82 of the wedge 74 approaches close to the staple 18, which may be already completely or substantially completely deformed against the anvil 32. Alternately, deformation of the staple 18 may continue to the point where the peak 82 of the wedge 74 contacts the staple 18. When the peak 82 reaches or comes close to the staple 18, the force exerted on the staple 18 is primarily in the upward direction. Further, this force is exerted on the staple 18 at a location at or in proximity to the tab 28 that connects the staple 18 to the feeder belt 16. That force shears, breaks or otherwise separates the staple 18 from the feeder belt 16. The tab 28 is configured such that the force exerted by the peak 82 of the wedge 74, or by a portion of the wedge 74 in proximity to the peak 82, is sufficient to shear, break or otherwise separate the staple 18 from the feeder belt 16. Where the staple 18 and/or tab 28 include a weakened area at or near their intersection, the staple 18 may shear, break or otherwise separate from the feeder belt 16 at that weakened area. The peak 82 may also actively push, urge or otherwise eject the staple 18 completely out of the housing 60. Alternately, the staple 18 is passively ejected from the housing 60, meaning that the staple 18 is not affirmatively urged out of the housing 60; rather, it is simply released from the housing 60 and allowed to exit therefrom. At this point, the deformed and ejected staple 18 is in position in the blood vessel 148. The frangibility of the staples 18 allows the staples 18 to be held securely and reliably by the feeder belt 16, and thus by the staple holder 30, while providing for reliable separation and deployment. The second surface 80 does not substantially contact the staple 18 or tab 28. Alternately, the second surface 80 may be shaped or otherwise configured to assist in deformation and/or ejection of the staple 18.

As another example, the wedge 74 may be configured as shown in FIG. 28. As stated above, the first segment 140 of that wedge 74 may be shaped to facilitate deployment of the staple 18, and the second segment 142 of that wedge 74 may be shaped to facilitate shearing or otherwise separating the staple 18 from the feeder belt 16. As the wedge 74 is moved relative to a staple 18 and contacts that staple 18, the first segment 140 of the wedge 74 encounters the staple 18 and applies a force to that staple 18 proximally and upward to form that staple 18, substantially as described above. The first segment 140 may be shaped such that formation of the staple 18 is substantially complete by the time the first segment 140 of the wedge 74 has moved out of contact with the staple 18. The second segment 142 may have a shape that facilitates separation of the formed staple 18 from the feeder belt 16. As the wedge 74 continues to move proximally, the first surface 140 moves out of contact with the staple 18, which is substantially formed, and the second surface 142 moves into contact with that substantially-formed staple 18. Where the staple 18 is shaped such as shown in FIGS. 25-27, after that staple 18 has been substantially formed, the bump 136 in that staple 18 may be oriented generally downward and in the path of travel of the second surface 142. Thus, as the second surface 142 slides proximally, it applies a force upward against the bump 136, where that force shears, breaks or otherwise separates the formed staple 18 from the feeder belt 16.

After the staple 18 has been separated from the feeder belt 16, the wedge 74 may continue its motion in the proximal direction. As it does so, it encounters another staple 18, and deforms that staple 18 and separates that staple 18 from the feeder belt 16 in substantially the same manner as described above. The wedge 74 may be long enough that, as the wedge 74 has deformed one staple 18 a substantial amount but that staple 18 has not yet separated from the feeder belt 16, the wedge 74 engages and begins to deform the next most distal staple 18. Alternately, the wedge 74 is short enough that it completely deforms one staple 18, which is then ejected, before the wedge 74 engages and begins to deform the next most distal staple 18.

The block 84 may be controlled to move each wedge assembly 72 and corresponding wedge 74 longitudinally along a fixed distance, such that a fixed number of staples 18 is deployed by each wedge 74 during each actuation. As a result, referring also to FIG. 29, the length of each staple line 146 in a blood vessel 148 or other tissue is fixed. The term "staple line" refers to the grouping of staples 18 in a row 26 after their ejection into tissue. The block 84 may be controlled to move along a fixed distance in any suitable manner. As one example, the rod 104 is movable proximally along that fixed distance during each actuation of the endocutter 2. Each fixed number of staples 18 in a row 26 may be grouped together and separated from an adjacent group of staples 18 by a blank space on the feeder belt 16, where that blank space may have any suitable length. The blank space allows the wedge 74 to be long enough in the longitudinal direction to engage and begin to deform a second staple 18 while that wedge 74 is still completing the deformation and/or ejection of the previous staple 18. Thus, when the wedge 74 moves proximally far enough to encounter the blank space, no staple 18 is present for that wedge 74 to deform, such that the wedge 74 can complete deformation of each staple 18 in the group without leaving a subsequent staple 18 partially deformed. However, the wedge may be short enough that it completely deforms one staple 18, which is then ejected, before the wedge 74 engages and begins to deform the next most distal staple 18.

Alternately, the block 84 may be selectively controlled to move each wedge assembly 72 and corresponding wedge longitudinally along a selectable distance, such that a selected number of staples 18 may be deployed by each wedge 74 during actuation. In this way, the length of the staple line 146 in a blood vessel 148 or other tissue is variable, and selectable by the user. The block 84 may be selectively controlled in any suitable manner. As one example, the rod 104 is movable proximally along a distance selectable by the user during each actuation of the endocutter 2. The rod 104 may be actuated to move along that selected distance by the handle 8, which also may be configured to receive user input related to the selected distance. The handle 8 may be configured in any suitable manner to control the longitudinal distance of travel of the rod 104. As one example, the handle 8 may include a stepper motor attached to the rod 104 that translates the rod 104 a selected one of a discrete number of lengths. As another example, the handle 8 may include a mechanical stop that is movable by the user, where the rod 104 stops its proximal motion when it encounters the mechanical stop. That is, the rod 104 may be spring-loaded or biased across a distance at least as long as the longest selectable staple line 146, and the mechanical stop is used to stop travel of the rod 104 at a distance less than the longest selectable staple line 146. Because the distance across which the wedge 74 travels may vary during each actuation and is user selectable, advantageously no blank spaces are present in each feeder belt 16. In addition, the wedge advantageously may be short enough that it completely deforms one staple 18, which is then ejected, before the wedge 74 engages and begins to deform the next most distal staple 18.

Referring to FIGS. 11-12 and 14-17, as the block 84 moves proximally, it also moves the knife 90, which is connected to the block 84 via the hook 92 or other structure at the proximal end of the knife 90. As the knife 90 moves proximally, it cuts the tissue held between the anvil 32 and the staple holder 30. The knife 90 may cut that tissue while the staples 18 are being deformed and ejected. As the knife 90 moves proximally from its initial position, the bottom of the blade 108 of the knife 90 may engage and ride up the ramp 116 at the distal end of the retainer 112. As the blade 108 rides up the ramp 116, at least part of the cutting edge 110 of the blade 108 moves above the top plates 66 of the housing and begins to cut tissue held between the anvil 32 and the staple holder 30. After the blade 108 reaches the top of the ramp 116, it continues to move proximally along the upper surface of the extension 114 as the block 84 continues to pull the knife 90 proximally. At least part of the blade 108 may slide between the inner walls 68 of the housing as the knife 90 is pulled proximally. Alternately, the blade 108 may be completely above the inner walls 68 of the housing, or may move in a different manner. Alternately, the ramp 116 and the extension 114 may be omitted, and the cutting edge 110 of the blade 108 may be controlled to rise above the top plates 66 of the housing 60 in another manner. Alternately, the blade 108 may be controlled to move substantially only in the longitudinal direction, such that the blade 108 does not substantially move in the vertical direction.

Figure 29:
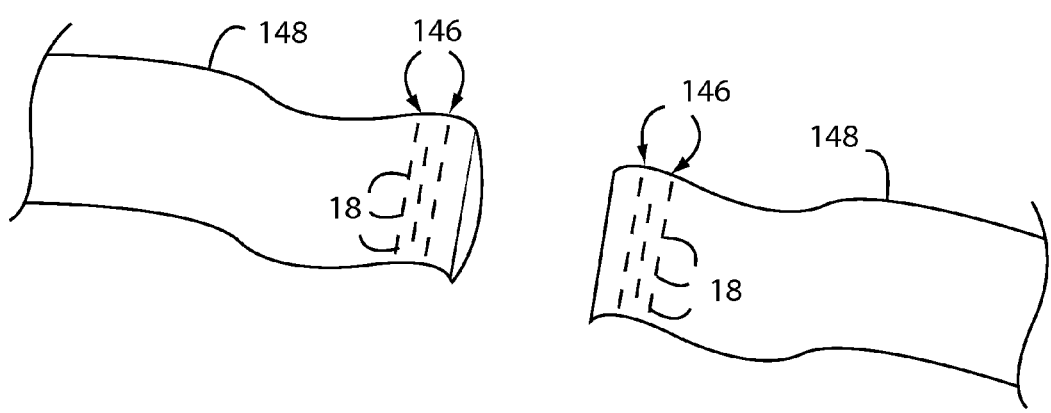
FIG. 29 is a perspective view of a blood vessel after transection by an endocutter.

After the fixed or selected number of staples 18 have been deformed and ejected, motion of the block 84 stops. When motion of the block 84 stops, the block 84, wedges 74 and blade 108 are each in a final position. The blade 108 is sized and shaped such that the blade 108 has completely cut through the tissue held between the anvil 32 and the staple holder 30 when the blade 108 is in the final position. In the final position, at least one wedge 74 and/or the blade 108 may be proximal to the corresponding receiving space 70 in the housing 60. Alternately, the wedges 74 and/or blade 108 may remain within the corresponding receiving space 70 in the housing 60 in their final position. After the fixed or selected number of staples 18 have been deformed and ejected, and the cutting edge 110 of the blade 108 has transected the tissue held between the anvil 32 and the staple holder 30, the end effector 4 is returned to its open position, releasing the tissue. Referring also to FIG. 29, where that tissue is a blood vessel 148, the blood vessel 148 has been transected into two segments, each of which has staggered rows of staples 18 forming a staple line 146 near an end thereof. Each wedge 74 actuated staples 18 in the corresponding row 26, and as set forth about the staples 18 and the apertures 67 in the top plate 66 of the housing 60 are staggered. By staggering the rows 26 of staples 18 in a staple line 146, hemostasis at the end of the blood vessel 148 is facilitated, because the leak path is longer in length and more convoluted than if the rows 26 of staples 18 were not staggered.

As another example of actuation of the endocutter 2, the wedge 74 may be initially proximal to the staples 18 in the corresponding row 26, and the wedge 74 is moved distally rather than proximally to deploy one or more staples 18 in that row 26. Such distal motion of the wedge 74 may be caused by, for example, moving the rod 104 in the distal direction. Where the wedge 74 is moved distally to deploy staples 18, the first surface 79 and the second surface 80 of the wedge 74 may be shaped differently in order to deploy the staples 18 properly. Further, the staples 18 may be oriented backward relative to the feeder belt 16, such that the free end 22 of each staple 18 is located distal to the point of attachment between the staple 18 and the feeder belt 16. The other aspects of operation of the staple holder 30 also are performed substantially in reverse order from the order described above, in order to deform the staples 18 and separate them from the feeder belt 16.

Next, the endocutter 2 may be fired again, without removing the end effector 4 from the patient, changing a cartridge or other disposable staple holder, or reloading the end effector 4 from outside the endocutter 2. To do so, the handle 8 may be actuated to return the block 84 to its initial position after the end effector 4 has been returned to its open position. Alternately, the block 84 is returned to its initial position when the end effector 4 returns to its open position, or at a different time. The rod 104 may be moved in the proximal direction to return the block 84 to its initial position. Alternately, the block 84 may be returned to its initial position in any other suitable manner. As one example, the block 84 may be biased distally, such that the rod 104 may be released and the block 84 automatically returns to the initial position. As another example, the block 84 may be biased proximally, such that the rod 104 is not affirmatively moved proximally to deploy and eject the staples 18. If so, the rod 104 then may be used to push the block 84 distally to its initial position and hold the block 84 in that initial position. Alternately, the block 84 may be returned to its initial position in any other suitable manner. As the block 84 moves back to its initial position, it moves the wedges 74 and the blade 108 back to their initial positions, reversing the paths traveled by the wedges 74 and blade 108 during actuation of the end effector 4. Alternately, the wedges 74 and/or blade 108 may move in a different manner and/or along a different path to return to their initial positions. Because the staples 18 that would otherwise be in the path of the wedges 74 have been deployed out of the housing 60, the wedges 74 may return to their initial position substantially without interference. Further, because the tissue has been released from the end effector 4, the blade 108 returns to its initial position substantially without contacting tissue.

At this point, the wedges 74 and blade 108 are in their initial positions. Next, if the feeder belt 16 was restrained against motion during the previous actuation of the end effector 4 by the sliding clamps 160, those sliding clamps are returned to the first position, in which the upper clamp 162 does not restrain the feeder belt 16. Such motion may include sliding the upper clamp 162 distally and/or sliding the lower clamp 164 proximally. During the sliding motion, the tongue 168 of the upper clamp 162 slides along the slot 166 of the lower clamp 164. As the upper clamp 162 and/or lower clamp 164 slide, the cam surfaces 170, 172 engage one another to cause the upper surface of the upper clamp 162 to move downward out of contact with the feeder belt 16, to allow the feeder belt 16 to advance. If a different or additional restraint such as a brake or clutch in the handle 8, shaft 6 or end effector 4 was used, that restraint is released. The feeder belt 16 is then moved in order to advance fresh staples 18 into the housing 60. This motion of the feeder belt 16 may be referred to as "advancing" the feeder belt 16, regardless of the fact that some or all of the feeder belt 16 may be moved in a direction other than distally during that advancing. Advancing the feeder belt 16 may be accomplished in any manner. As one example, as set forth above, a feeder belt 16 is routed around each nose 50, along a path that starts generally straight and in the distal direction, then is curved along the surface of the corresponding nose 50, and then is generally straight and in the proximal direction, such that the nose 50 changes the direction of motion of the corresponding feeder belt 16 from generally distal to generally proximal. The portion of the feeder belt 16 located under and proximal to the nose 50 may be retracted proximally, thereby pulling the portion of the feeder belt 16 located above and proximal to the nose 50 in the distal direction and advancing fresh staples 18 into the housing 60. The portion of the feeder belt 16 located under and proximal to the nose 50 may be retracted proximally in any suitable manner. As one example, that portion of the feeder belt 16 may extend into the handle 8, where a gear, roller or other mechanism exerts a force directly on the feeder belt 16. As another example, the feeder belt 16 may be connected to an intermediate structure or mechanism that extends into the handle 8 and upon which a force is exerted. As another example, referring also to FIG. 25, one or more openings 132 in the feeder belt 16 are engaged by one or more gears, pins or other mechanisms, such that engagement with the openings 132 is used to advance the feeder belt 16. As another example, any other suitable mechanism, structure or method may be used to move the feeder belt 16 in order to advance fresh, undeployed staples 18 into the housing 60. Where the feeder belt 16 is movable generally linearly, and the nose 50 is not utilized, the housing 60 may be longer, and the feeder belt 16 is simply advanced or retracted generally linearly in order to advance fresh staples 18 into the housing 60.

The feeder belt 16 may be advanced with or without feedback. As an example of advancing the feeder belt 16 without feedback, a stepper motor or other mechanism may be used to advance the feeder belt 16 a fixed distance each time. Where feedback is provided, the feeder belt 16 is advanced a distance that is related to the feedback; that distance may not be fixed every time. As one example, a pinwheel (not shown) may be configured to engage the openings 132 in the feeder belt 16 with pins, such that motion of the feeder belt 16 causes the pinwheel to rotate. Such rotation of the pinwheel may produce mechanical or electrical feedback that is transmitted mechanically or electrically to the handle 8, such that advancement of the feeder belt 16 continues until the pinwheel has rotated a particular amount. In this way, the pinwheel provides confirmation that the feeder belt 16 has in fact advance to a position in which unfired staples 18 are in position in the housing 60 at locations corresponding to the apertures 67 in the top plates 66 of the housing 60. As another example of feedback, an optical sensor or sensors (not shown) may be positioned in the end effector 4 to sense the openings 132, such that the optical sensor or sensors can determine the degree of advancement of the feeder belt 16. As another example, any other suitable mechanism may be used to generate feedback and to transmit that feedback in mechanically, electrically and/or as data to a suitable controller, which may be located in the handle 8 or in any other portion of the endocutter. The controller may be a cam, an integrated circuit, a microprocessor, an analog circuit or circuits, a digital circuit or circuits, a mechanical computer, or any other suitable controller The wedges 74 and blade 108 are in the initial position, and unfired staples 18 are in position in the housing 60 at locations corresponding to the apertures 67 in the top plates 66 of the housing 60. The feeder belt 16 may be held substantially in place, either passively such as by friction with the corresponding nose 50, or actively such as by a brake or clutch (not shown) in the handle 8, shaft 6 and/or end effector 4. At this time, the end effector 4 is configured for actuation again, and is in an initial configuration substantially as described above. The end effector 4 may then be actuated again, substantially as described above. In this way, the end effector 4 may be actuated multiple times without removing the end effector 4 through the trocar port 10 or other incision, structure or mechanism that allows access to the interior of the body of the patient. Keeping the end effector 4 within the body of the patient without withdrawing that end effector 4 through the trocar port 10 or other incision, structure or mechanism that allows access to the interior of the body of the patient may be referred to as maintaining the end effector within the body of the patient. The endocutter 2 may be actuated multiple times within the patient, without being removed from the patient, until the staples 18 in the endocutter 2 are exhausted. An indicator may be provided in the handle 8 or at another location in the endocutter 2 that shows how many unfired staples 18 remain in the endocutter 2.

Actuation of the endocutter 2 above has been generally described in terms of deployment and ejection of a single row 26 of staples 18 for clarity, where that deployment and ejection may be performed in substantially the same manner along each row 26 of staples 18. Operation of the endocutter 2 may be substantially as described above with regard to any number of rows 26 of staples 18 on a feeder belt 16. That is, an endocutter 2 having two rows 26 of staples 18 on a feeder belt 16, or more than three rows of staples 18 on a feeder belt 16, may be actuated substantially as described above.

Driverless Endocutter and Operation

Optionally, referring to FIGS. 12, 13 and 28, the wedges 74 may be fixed in place relative to the staple holder 30. For example, the wedges 74 may simply be molded, cut, formed or otherwise fabricated as part of the feeder belt guide 40 or other component of the end effector 4. As each feeder belt 16 is advanced, the most distal unformed staple 18 in each row 26 contacts the stationary wedge 74. The feeder belt 16 then does not stop, but continues to move. As the feeder belt 16 continues to advance, the relative motion between the feeder belt 16 and the stationary wedge 74 causes the staple 18 to deform and then separate from the feeder belt 16, in substantially the same manner as described above with regard to motion of the wedge 74 relative to the substantially stationary feeder belt 16. Where the wedges 74 are stationary, the end effector 4 does not apply a row of staples 18 longitudinally along a staple line. Instead, the end effector 4 sequentially deploys the distalmost staple 18 in each row 26 as the feeder belt 16 pulls that staple 18 onto the corresponding wedge 74.

Alternately, for a single-use device, a number of wedges 74 equal to the number of staples 18 to be deployed are fabricated as part of the end effector 4, and are each located immediately proximal or distal to the corresponding staple 18. As the feeder belt 16 is moved longitudinally, each staple 18 contacts the corresponding fixed wedge 74, deforms to a closed configuration, and then separates from the feeder belt 16. In this way, two or more staples 18 can be deployed along a staple line at the same time, without the use of wedge assemblies 72. Optionally, the wedges 74 may be movable downward or in another direction from a first position after deploying the staples 18, such that a feeder belt 16 can be advanced to place new, undeployed staples 18 in position for firing, after which the wedges 74 may be moved back to their first position.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical endocutter, comprising:
   a staple holder;
   at least one feeder belt with at least one substantially planar segment having two lateral edges, at least part of said at least one feeder belt extending into said staple holder; and
   a plurality of staples, wherein each staple comprises a first end frangibly affixed to a corresponding one of said at least one feeder belt, wherein each of said first ends is affixed to said feeder belt at a location laterally spaced from a longitudinal centerline of said feeder belt, and a second free end, wherein said staples form at least one row, each row including at least two of said staples; wherein said staples in at least one said row are staggered relative to said staples in at least one other said row; wherein at least one of said staples is affixed to and is out of plane relative to said substantially planar segment of said feeder belt; and wherein at least one row of staples is frangibly connected to a corresponding one of said two lateral edges of said at least one feeder belt.

2. A surgical endocutter, comprising:
   a feeder belt;
   a plurality of staples frangibly connected to said feeder belt; and
   at least one wedge movable relative to said staples in a direction substantially longitudinal relative to said feeder belt; wherein at least one said wedge both directly engages a plurality of said staples and disconnects a plurality of said staples from said feeder belt in a single continuous motion of said wedge.

3. The surgical endocutter of claim 2, wherein at least one said wedge serially engages said staples and serially disconnects said staples from said feeder belt.

4. A surgical endocutter, comprising:
   an anvil;
   a feeder belt including multiple tabs extending laterally therefrom;
   a staple holder that holds at least part of said feeder belt, said staple holder connected to said anvil;
   a plurality of staples frangibly connected to said tabs; and
   at least one wedge movable relative to said staples in a direction substantially longitudinal relative to said feeder belt; wherein said at least one wedge both directly engages a plurality of said staples and also disconnects a plurality of said staples from said tabs of said feeder belt in a single continuous motion of said wedge; and wherein engagement between said at least one wedge and said plurality of staples causes each staple of said plurality of staples to rotate about a corresponding one of said tabs to which it is frangibly connected, contact said anvil, and deform to a closed configuration.

5. The surgical endocutter of claim 4, wherein engagement between said at least one wedge and said plurality of staples causes each staple to deform plastically.

\* \* \* \* \*